(12) United States Patent
Takizawa et al.

(10) Patent No.: US 9,081,075 B2
(45) Date of Patent: Jul. 14, 2015

(54) MAGNETIC RESONANCE IMAGING APPARATUS AND MAGNETIC RESONANCE IMAGING METHOD

(75) Inventors: Masahiro Takizawa, Tokyo (JP); Hiroyuki Itagaki, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 747 days.

(21) Appl. No.: 12/747,439

(22) PCT Filed: Dec. 16, 2008

(86) PCT No.: PCT/JP2008/072804
§ 371 (c)(1),
(2), (4) Date: Jun. 10, 2010

(87) PCT Pub. No.: WO2009/081785
PCT Pub. Date: Jul. 2, 2009

(65) Prior Publication Data
US 2010/0260403 A1 Oct. 14, 2010

(30) Foreign Application Priority Data

Dec. 25, 2007 (JP) ................................ 2007-331967

(51) Int. Cl.
*G06K 9/00* (2006.01)
*G01R 33/561* (2006.01)
(Continued)

(52) U.S. Cl.
CPC ............ *G01R 33/5615* (2013.01); *A61B 5/055* (2013.01); *G01R 33/4818* (2013.01); *G01R 33/543* (2013.01); *G01R 33/546* (2013.01); *G01R 33/5616* (2013.01)

(58) Field of Classification Search
CPC . G01R 33/4818; G01R 33/5615; A61B 5/055
USPC .................................................. 382/131, 128
See application file for complete search history.

(56) References Cited

U.S. PATENT DOCUMENTS 6,430,430 B1 * 8/2002 Gosche .......................... 600/410
6,459,922 B1 * 10/2002 Zhang ............................ 600/410
(Continued)

FOREIGN PATENT DOCUMENTS

JP 2001-149340 6/2001
JP 2001-161657 6/2001
(Continued)

OTHER PUBLICATIONS

Tan, C. S. (2011). Magnetic resonance elastography using a single-sided constant gradient magnet (Order No. MR81708). Available from ProQuest Dissertations & Theses Full Text: Science & Technology. (916901381). Retrieved from http://search.proquest.com/docview/916901381?accountid=14753.*
(Continued)

*Primary Examiner* — Mark Holcomb
(74) *Attorney, Agent, or Firm* — Cooper & Dunham LLP

(57) ABSTRACT

An image in which an area of interest on an image is optimally susceptibility-emphasized is obtained in susceptibility-emphasized imaging. A measuring order of plural echo signals is controlled in accordance with the size of a desired area of interest of an examinee. Preferably, a target frequency in a K space is determined in accordance with the size of the area of interest, and the measuring order of plural echo signals is controlled so that an echo signal corresponding to the target frequency is measured at a target echo signal or in the neighborhood of the target echo time.

15 Claims, 13 Drawing Sheets

(51) Int. Cl.
*A61B 5/055* (2006.01)
*G01R 33/48* (2006.01)
*G01R 33/54* (2006.01)

(56) References Cited

U.S. PATENT DOCUMENTS

| | | | | |
|---|---|---|---|---|
| 6,501,272 | B1* | 12/2002 | Haacke et al. | 324/306 |
| 6,658,280 | B1* | 12/2003 | Haacke | 600/410 |
| 6,792,257 | B2* | 9/2004 | Rabe | 455/277.1 |
| 8,072,215 | B2* | 12/2011 | Fuderer | 324/318 |
| 2003/0052676 | A1 | 3/2003 | Takahashi et al. | |
| 2008/0071167 | A1* | 3/2008 | Ikedo et al. | 600/419 |
| 2009/0278535 | A1* | 11/2009 | Takizawa et al. | 324/309 |
| 2010/0072994 | A1* | 3/2010 | Lee et al. | 324/307 |
| 2010/0195885 | A1* | 8/2010 | Ma | 382/131 |

FOREIGN PATENT DOCUMENTS

| | | |
|---|---|---|
| JP | 2003-144413 | 5/2003 |
| JP | 2004-89515 | 3/2004 |
| WO | WO 2006118110 A1 * | 11/2006 |

OTHER PUBLICATIONS

Haacke et al. (Aug. 23, 2004), "Susceptibility Weighted Imaging (SWI)", Magnetic Resonance in Medicine, vol. 52, pp. 612-618.
International Search Report in PCT/JP2008/072804.

* cited by examiner

FIG. 2
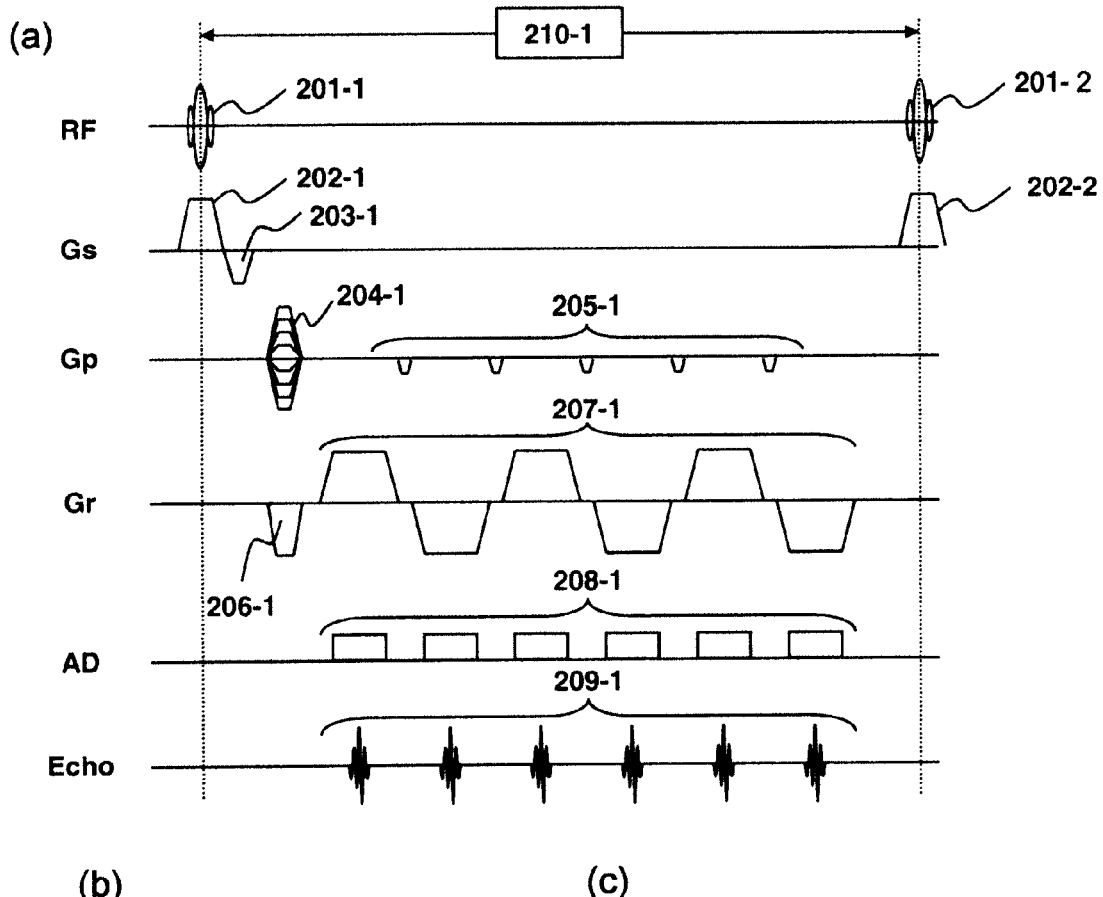
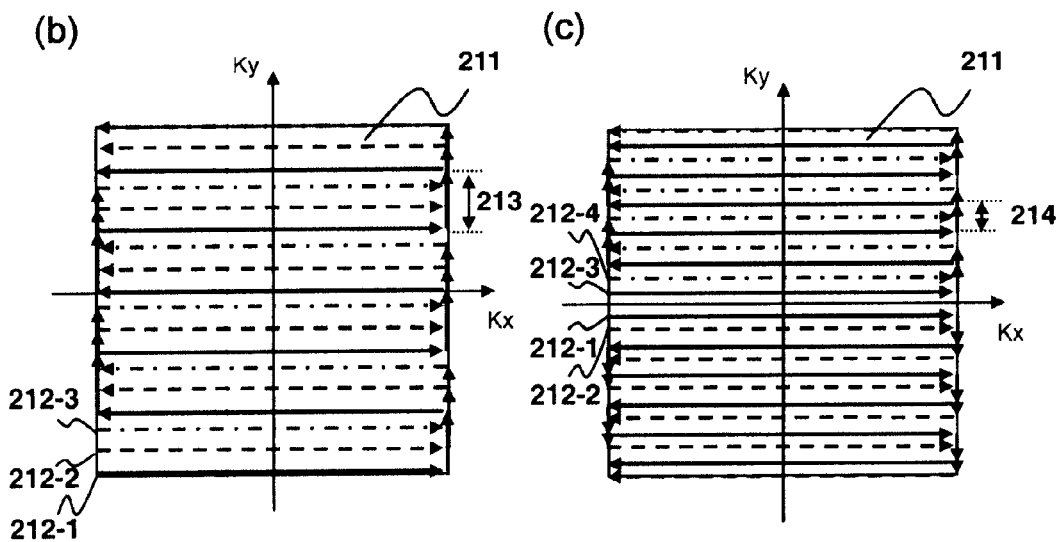

FIG. 3
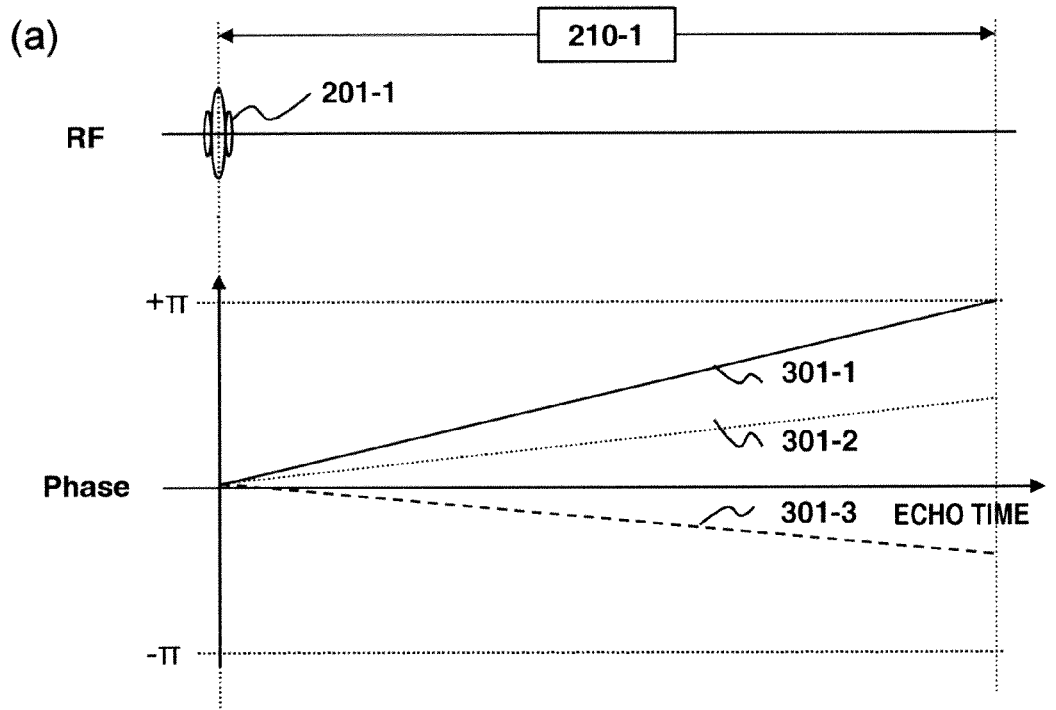
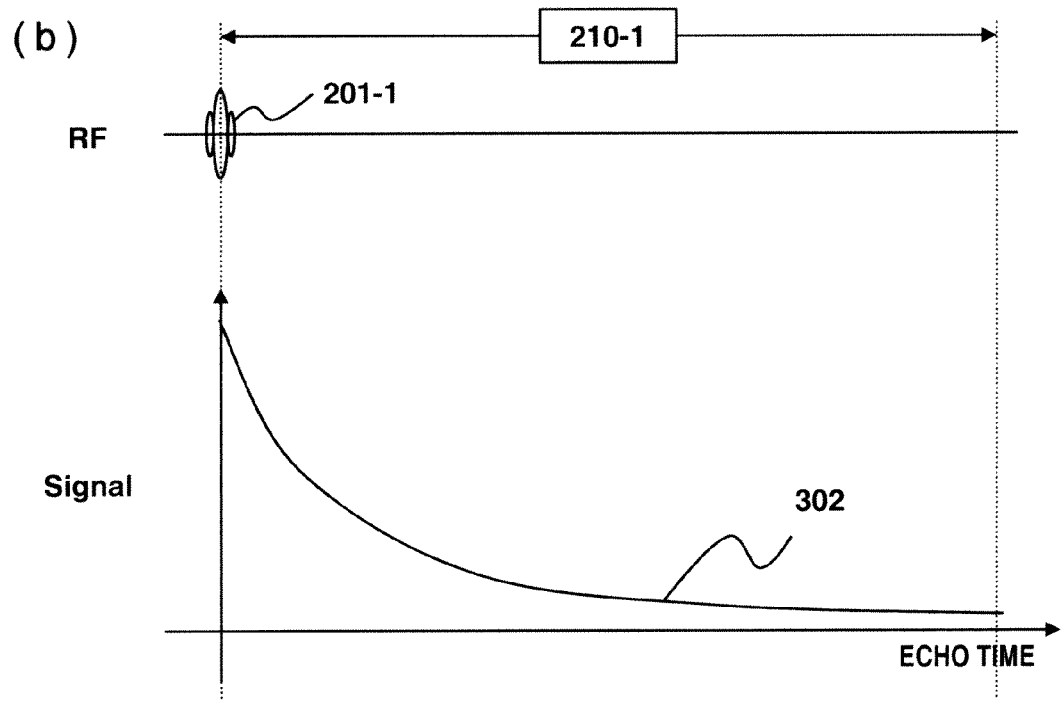

FIG 9
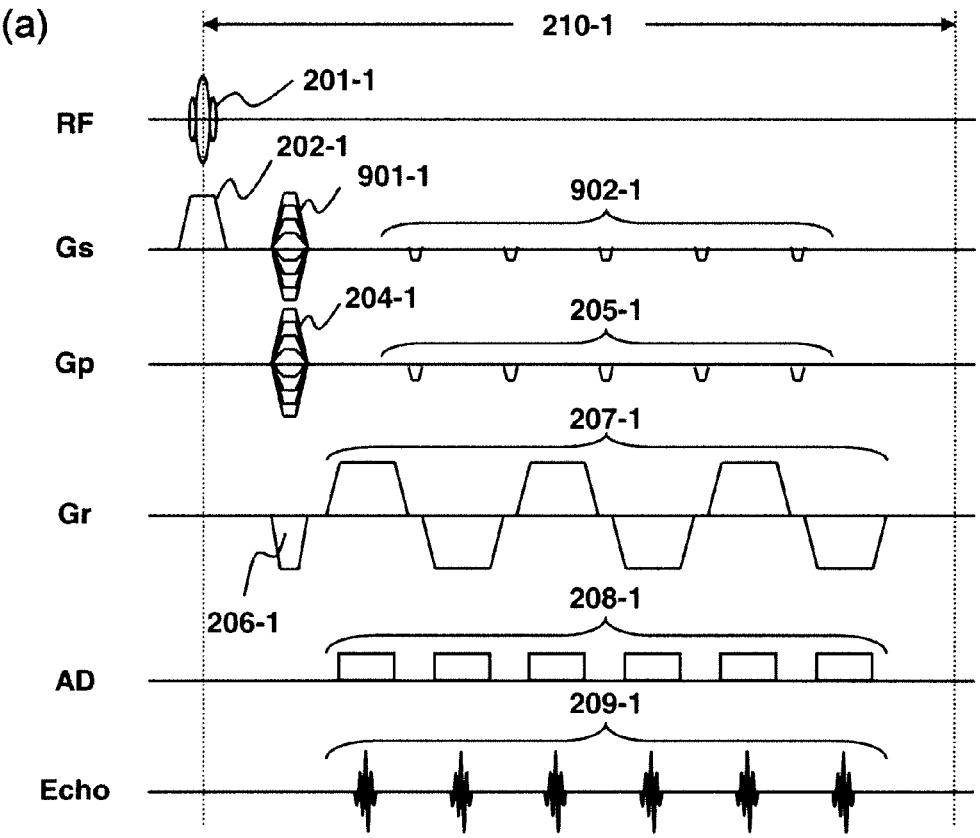
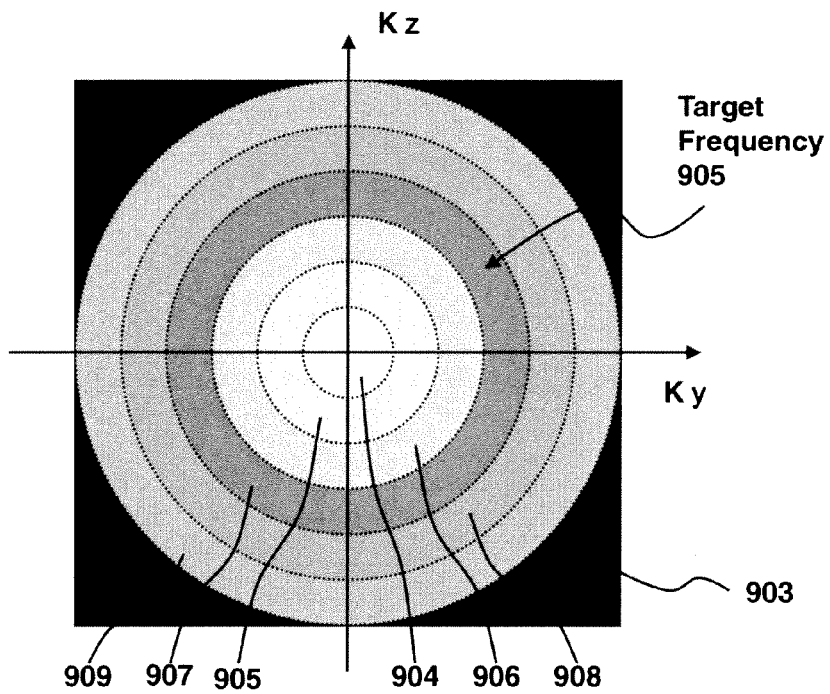

FIG. 10
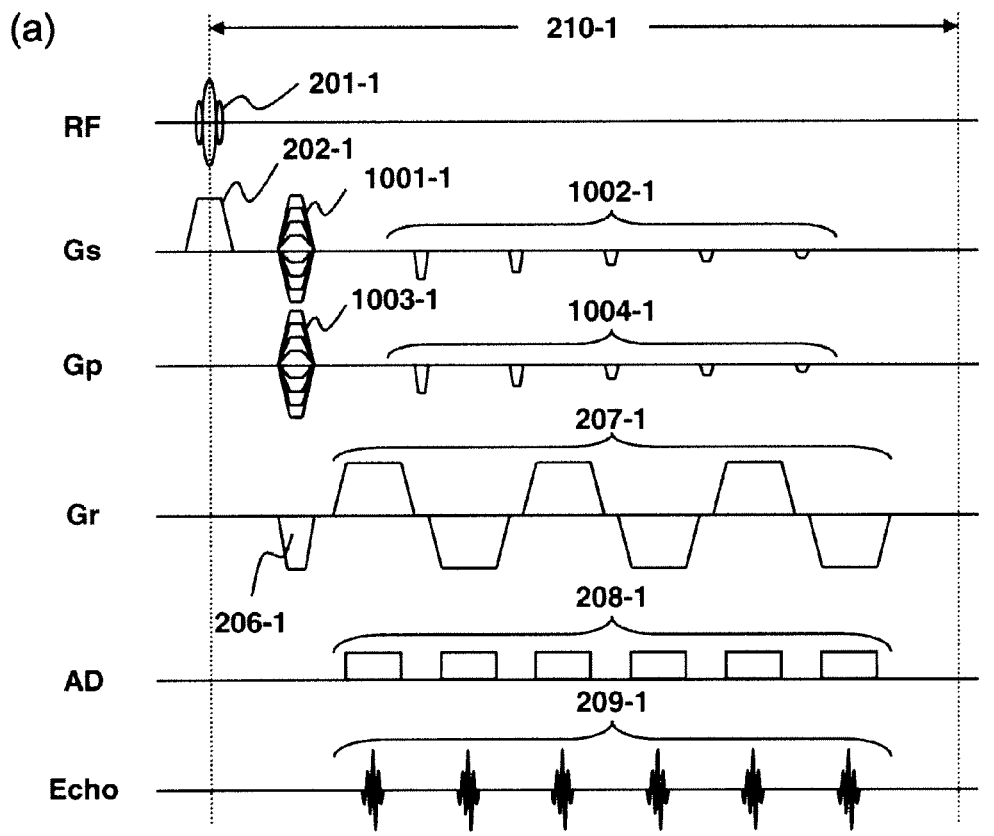
(a)
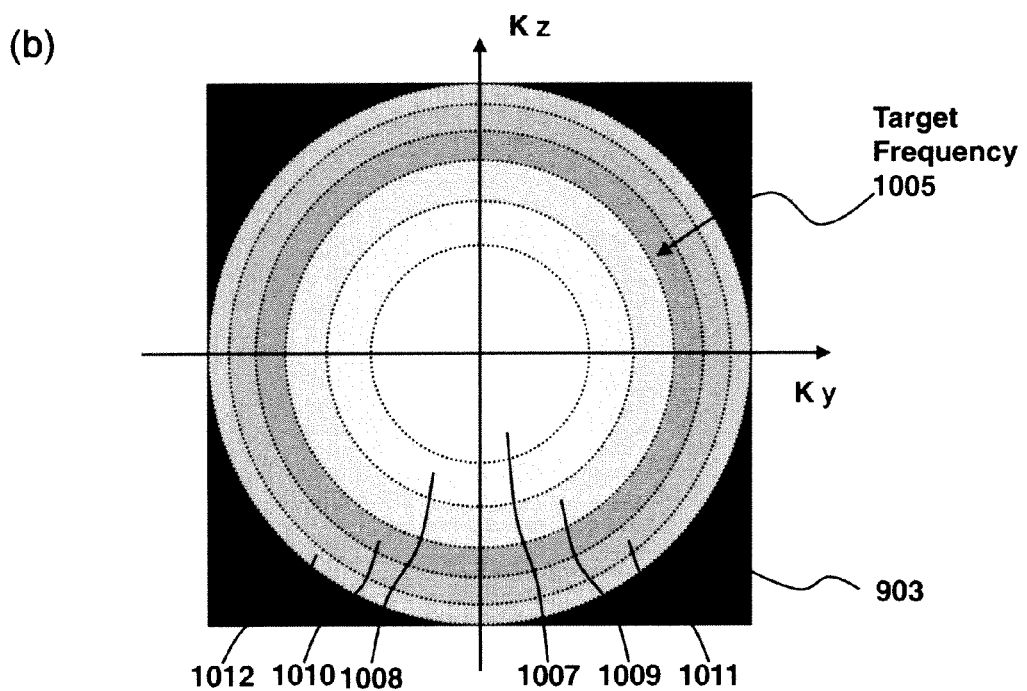
(b)

FIG. 12
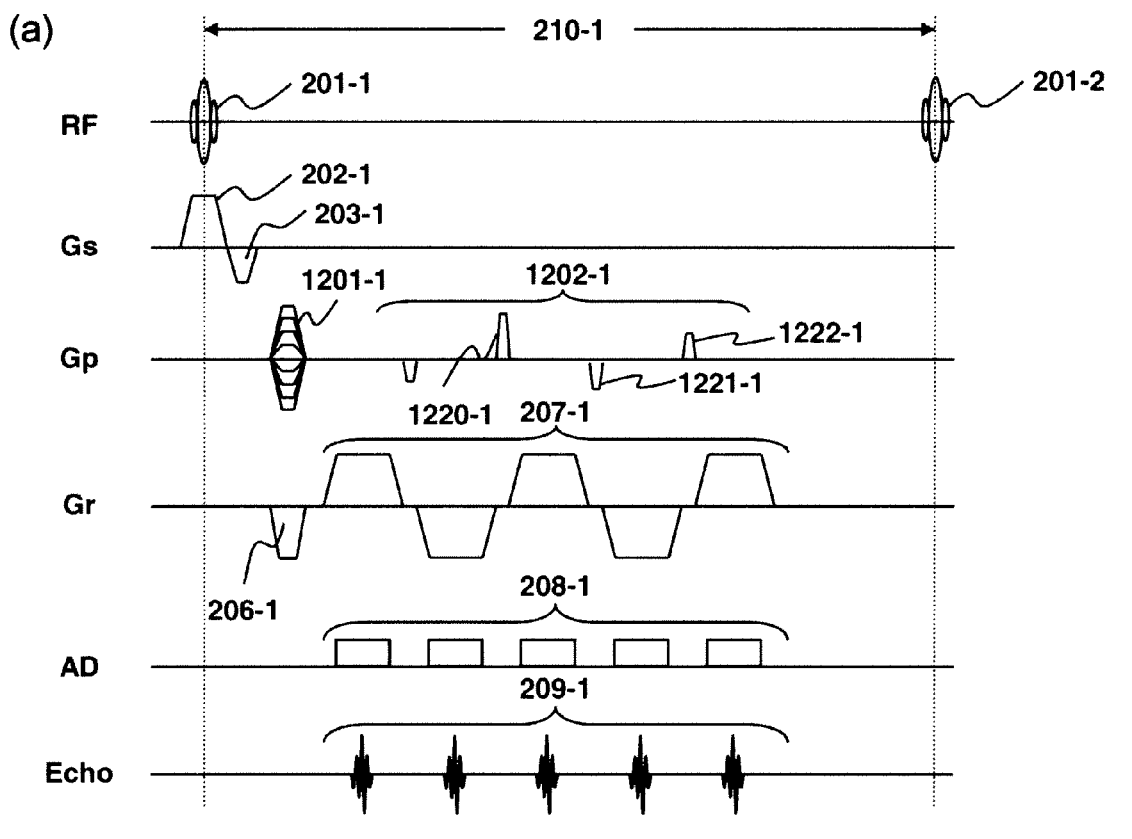
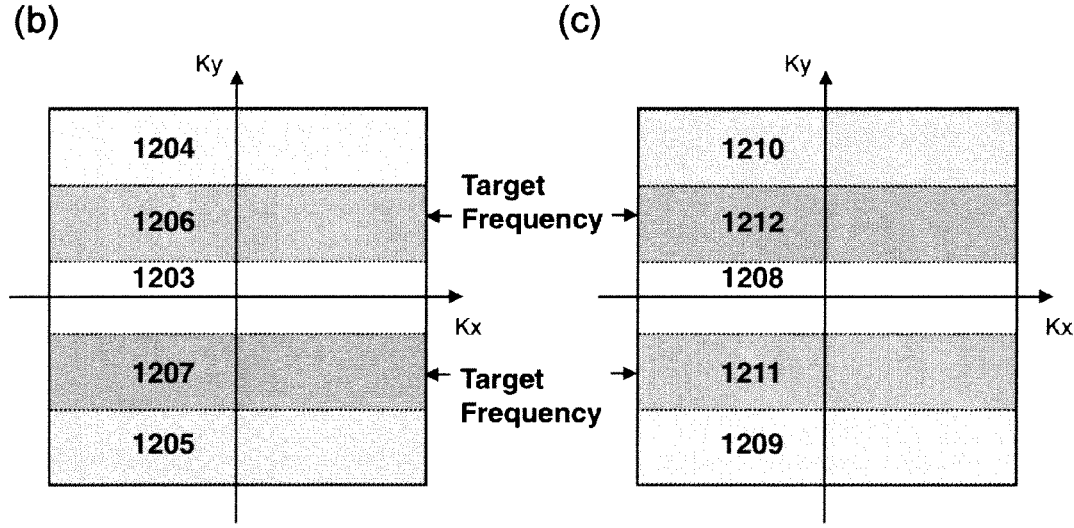

| SITE | MINIMUM TARGET SIZE | MAXIMUM TARGET SIZE |
|---|---|---|
| HEAD PORTION A | 0.5mm | 3.0mm |
| HEAD PORTION B | 0.2mm | 2.0mm |
| CERVICAL PART A | 1.0mm | 3.0mm |
| CERVICAL PART A | 0.5mm | 1.5mm |
| ABDOMINAL PART A | 1.0mm | 5.0mm |
| .. | .. | .. |
| .. | .. | .. |
|  |  |  |

MAGNETIC RESONANCE IMAGING APPARATUS AND MAGNETIC RESONANCE IMAGING METHOD

TECHNICAL FIELD

The present invention relates to a technique for obtaining a susceptibility-emphasized image at high speed by using a magnetic resonance imaging (hereinafter referred to as MRI) apparatus for obtaining a tomogram of an examination site of an examinee by using nuclear magnetic resonance phenomenon.

BACKGROUND ART

The MRI apparatus uses uniform magnetostatic field, and the magnetostatic field locally varies due to the magnetic susceptibility of an examinee. The effect of the local magnetic field variation appears as phase variation in image data. There is known an imaging method for emphasizing this phase variation through calculation processing (hereinafter referred to as susceptibility-emphasized imaging) (patent document 1). Attention has been paid to this susceptibility-emphasized imaging as an effective method to MR angiography of vein because the magnetic susceptibility can be emphasized based on deoxy hemoglobin in blood.

However, the susceptibility-emphasized imaging uses the phase variation caused by the magnetic susceptibility, and thus it requires an echo signal at the time point when about 70 ms elapses from the irradiation time of an RF pulse. Therefore, the repetitive time (TR) of a pulse sequence (hereinafter merely abbreviated as sequence) cannot be set to a short time, and thus the imaging time is increased.

Furthermore, a method of measuring plural echo signals with one RF pulse shot is known as a method of shortening the imaging time in the MRI apparatus, and an echo planar (EPI) method and a first spin echo (FSE) method are known as representative methods. An example of the susceptibility-emphasized imaging using the echo planar method to shorten the imaging time of the susceptibility-emphasized imaging is disclosed in (patent document 2).

Patent Document 1: U.S. Pat. No. 6,501,272
Patent Document 2: U.S. Pat. No. 7,154,269

DISCLOSURE OF THE INVENTION

Problem to be Solved by the Invention

However, when the echo planar method is applied to the susceptibility-emphasized imaging, information of an echo signal which is measured after lapse of a different time from the RF pulse irradiation is mixed with the phase variation of the image data.

Therefore, there is an unsolved problem that the emphasized effect based on the magnetic susceptibility is dispersed to the whole image and thus it is impossible to obtain an image in which an area of interest on an image is subjected to optimal susceptibility-emphasizing.

Therefore, the present invention has an object to obtain an image in which an area of interest on an image is optimally susceptibility-emphasized in susceptibility-emphasized imaging.

Means of Solving the Problem

In order to attain the above object, the present invention controls a measuring order of plural echo signals in accordance with the size of a desired area of interest of an examinee. Preferably, a target frequency in a K space is determined in accordance with the size of the area of interest and the measuring order of the plural echo signals is controlled so that the echo signal corresponding to the target frequency is measured at a target echo time or in the neighborhood thereof.

Specifically, an MRI apparatus of the present invention is characterized by comprising a measurement controller for controlling measurement of plural echo signals from an examinee on the basis of a predetermined pulse sequence, and a calculation processor for obtaining an image of the examinee on the basis of K space data in which data of plural echo signals are disposed in an K space, wherein the measurement controller controls a measuring order of plural echo signals in accordance with the size of a desired area of interest of the examinee.

Furthermore, an MRI method according to the present invention is characterized by comprising a measuring step of measuring plural echo signals from an examinee on the basis of a predetermined pulse sequence, and a calculation processing step of obtaining an image of the examinee on the basis of K space data in which data of plural echo signals are disposed in an K space, wherein the measuring step controls a measuring order of plural echo signals in accordance with the size of a desired area of interest of the examinee.

Effect of the Invention

As described above, according to the MRI apparatus and the MRI method of the present invention, an image in which an area of interest on an image is optimally susceptibility-emphasized can be obtained in susceptibility-emphasized imaging.

BEST MODE FOR CARRYING OUT THE INVENTION

Respective embodiments of an MRI apparatus according to the present invention will be described with reference to the drawings. In all the figures to describe the embodiments of the present invention, parts having the same functions are represented by the same reference numerals, and the duplicative description thereof is omitted.

First, an example of the MRI apparatus according to the present invention will be schematically described with reference to FIG. 1. FIG. 1 is a block diagram showing the overall construction of an example of the MRI apparatus of the present invention. The MRI apparatus obtains a tomogram of an examinee by using the nuclear magnetic resonance (NMR) phenomenon, and it comprises a magnetostatic field generating system 2, a gradient magnetic field generating system 3, a transmission system 5, a reception system 6, a signal processing system 7, a sequencer 4 and a central processing unit (CPU) 8 as shown in FIG. 1.

The magnetostatic field generating system 2 generates magnetostatic field in a space around an examinee 1 so that the magnetostatic field is uniform in a body axis direction or in a direction perpendicular to the body axis. Permanent magnet type, normal conduction type or superconduction type magnetic field generating means is disposed around the examinee 1.

The gradient magnetic field generating system 3 (gradient magnetic field generator) comprises gradient magnetic field coils 9 wound in three axial directions of X, Y and Z, and a gradient magnetic field power supply 10 for driving each of the gradient magnetic field coils 9. The gradient magnetic field power supply 10 for each of the coils is driven according to an instruction from the sequencer 4 described later, whereby gradient magnetic fields Gs, Gp and Gf in the three axis directions of X, Y, Z are applied to the examinee 1. More specifically, a slice selecting gradient magnetic field pulse (Gs) is applied to any one direction of X, Y, z to set a slice plane for the examinee 1, and a phase encode gradient magnetic field pulse (Gp) and a frequency encode (or readout) gradient magnetic field pulse (Gf) are applied in the other two directions, whereby position information in each direction is encoded into an echo signal.

The sequencer 4 is a measurement controller for repetitively applying a radio frequency magnetic field pulse (hereinafter referred to as "RF pulse") and a gradient magnetic field pulse at a predetermined sequence to control the measurement of the echo signal. The sequencer 4 is operated under the control of CPU 8, and transmits to the transmission system 5, the gradient magnetic field generator 3 and the reception system 6 various kinds of commands for measure echo signals required to reconstruct the tomogram of the examinee 1 to control these systems, thereby controlling the measurement of the echo signals.

The transmission system 5 irradiates an RF pulse to make atomic nucleus spins of atoms constituting a biomedical tissue of the examinee 1 excite nuclear magnetic resonance, and it comprises a radio frequency oscillator 1, a modulator 12, a radio frequency amplifier 13 and a radio frequency coil 14*a* at the transmission side. The radio frequency pulse output from the radio frequency oscillator 11 is amplitude-modulated by the modulator 12 at a timing based on an instruction of the sequencer 4, and the amplitude-modulated radio frequency pulse is amplified by the radio frequency amplifier 13, and supplied to a radio frequency coil 14*a* disposed in proximity to the examinee 1, so that the examinee 1 is irradiated with the electromagnetic wave (RF pulse).

The reception system 6 detects an echo signal (NMR) signal emitted due to nuclear magnetic resonance of atomic nucleus spins constituting a biomedical tissue of the examinee 1, and it comprises a radio frequency coil 14*b*, an amplifier 15, an orthogonal phase detector 16, and an A/D converter 17 at the reception side. An electromagnetic wave (NMR signal) of a response of the examinee 1 which is induced by an electromagnetic wave irradiated from the radio frequency coil 14*a* at the transmission side is detected by the radio frequency coil 14*b* disposed in proximity to the examinee 1 and amplified by the amplifier 15. Thereafter, the electromagnetic wave is divided into orthogonal signals of two systems by an orthogonal phase detector 16 at a timing based on an instruction from the sequencer 4, and the signals are respectively converted to digital amounts by an A/D converter 17 and transmitted to the signal processing system 7. The echo signal converted to the digital amount will be hereinafter referred to as data of echo signal or echo data.

The signal processing system 7 has external storage devices (storing means) such as an optical disc 19, a magnetic disk 18, and a display 20 comprising CRT or the like. When echo data input from the reception system 6 is input to CPU 8 (operation processor), CPU 8 executes operation processing such as signal processing, image reconstruction, displays a tomogram of the examinee 1 as a processing result on the display 20, and also records the tomogram into the magnetic disk 18 or the like of the external storage device. CPU 8 has a memory corresponding to a K space therein, and stores the echo data into the memory. The description representing that the echo signal or the echo data are disposed in the K space means that the echo data is written and stored into the memory.

The operating system 25 inputs various kinds of control information of the MRI apparatus and control information of the signal processing system 7, and it comprises a track ball or a mouse 23 and a keyboard 24. This operating system 25 is disposed in proximity to the display 20, and an operator interactively controls various kinds of processing of the MRI apparatus through the operating system 25 while watching the display 20.

In FIG. 1, the radio frequency coils 14*a* and 14*b* at the transmission side and the reception side and the gradient magnetic field coil 9 are disposed in the magnetostatic field space of the magnetostatic field generating system 2 in the space around the examinee 1.

Proton as a main constituent material of the examinee has been used as an imaging target spin species of the present MRI apparatus which has grown clinically popular. By imaging a spatial distribution of proton density or a spatial distribution of a relaxation phenomenon of an exciting state, the shape or function of a head portion, an abdominal area, four limbs or the like of a human body is imaged two-dimensionally or three-dimensionally.

Next, an example of the sequence of the echo planar (EPI) method provided to the MRI apparatus according to the present invention will be described with reference to FIG. 2. FIG. 2 is a sequence chart showing a sequence shape of the echo planar method of a gradient echo type multi-shot. Gs, Gp and Gr represent the axes of a slice selecting gradient magnetic field, a phase encode gradient magnetic field and a frequency encode gradient magnetic field, and RF, AD and Echo represent an RF pulse, a sampling window and an echo signal.

Furthermore, 201 represents an RF pulse, 202 represents the slice selecting gradient magnetic field pulse, 203 represents a slice refocus gradient magnetic field pulse, 204 represents a phase encode gradient magnetic field pulse, 205 represents a phase blip gradient magnetic field pulse group, 206 represents a frequency dephase gradient magnetic field pulse, 207 represents a frequency encode gradient magnetic field pulse group, 208 represents a sampling window group, and 209 represents an echo signal group. The sequencer 4 controls the transmission system 5, the gradient magnetic field generating system 3 and the reception system 6 on the basis of the sequence chart to measure an echo signal.

In the echo planar method, the sequencer 4 measures one echo signal 209 with respect to each readout gradient magnetic field pulse 207 with changing the polarity of the readout gradient magnetic field pulse 207 every irradiation of one RF pulse 201. This measurement is repetitively executed at a time interval 210 (repeat time TR), and echo signals whose number is required for reconstruct an image are measured. The number of echo signals required to reconstruct an image is generally set to about 64, 128 or 256 in accordance with a matrix of an image to be created. A numeral after "-" (hyphen) represents a repeat number. FIG. 2(*a*) shows a first sequence out of plural repeated sequences, and the second and subsequent repeated sequences are the same as the first sequence and thus the description thereof is omitted. In the sequence diagrams described below, numerals after -" (hyphen) has the same meaning.

As described above, according to the echo planar method, plural echo signals are measured by one RF pulse shot, and thus an image can be obtained at a higher speed as compared with a sequence of measuring one echo signal by one RF pulse shot. In the case of FIG. 2(*a*), six echo signals 209 are measured by one shot of RF pulse 201, and thus imaging can be performed at a sextuple high speed. A single-shot type echo planar method in which all the echo signals required to reconstruct an image can be measured by one shot RF pulse can further increase the imaging speed.

FIG. 2(b) is a schematic diagram showing an example of a K space 211 in which echo data measured by the echo planar method are disposed. The abscissa axis Kx of FIG. 2(b) corresponds to the time of the sampling window for an echo signal, and the ordinate axis Ky corresponds to the total amount of phase encode gradient magnetic field pulses applied to the phase encode axis at the time point when the echo signals are measured.

Arrows 212 in FIG. 2(b) represent an echo signal measuring order in the K space data obtained by using the echo planar method, and in this example, echo signals are sequentially measured from the lower side to the upper side in the Ky axial direction (that is, from the negative side to the positive side) (called as sequential ordering). Lines 212-1 (solid line), 212-2 (dashed line) and 212-3 (one-dotted chain line) correspond to echo signal groups 209-1, 209-2 and 209-3 measured at a repeat 210-1 (first of repeat), 210-2 (second of repeat, not shown) and 210-3 (third of repeat, not shown), and each line represents that an echo signal is measured every two other lines in the Ky axial direction.

In FIG. 2(b), a portion in which the arrow of each line 212 advances in parallel to the Kx axis corresponds to an echo signal, and six echo signals are contained in each line 212. The scan direction of the arrow at the echo signal position corresponds to the polarity of the readout gradient magnetic field pulse group 207. An interval 213 (214 in FIG. 2(c)) in the Ky direction between the arrows corresponds to the area of each phase blip gradient magnetic field 205, and the start position of each line 212 is changed by the phase encode gradient magnetic field pulse 204, whereby the K space can be arranged while the echo data are not overlapped with each other in the Ky direction.

FIG. 2(c) schematically shows another example of the K space 211 in which the echo data measured by the echo planar method are arranged. In this case, the K space is divided into two parts in the up-and-down direction (that is, positive and negative) with Ky=0 set as boundary, and the echo signals corresponding to the respective areas are measured (called as centric ordering). In this case, data of echo signal groups are continuously arranged at the upper side (positive side) and the lower side (negative side) of Ky=0. That is, the echo data of the echo signal groups 212-1 (solid line) and 212-2 (dotted line) are alternately arranged every other line in the Ky axis direction at the lower side while the echo data of the echo signal groups 212-3 (solid line) and 212-4 (one-dotted chain line) are alternately arranged every other line in the Ky axis direction at the upper side.

With respect to the thus-arranged two-dimensional K space data, two-dimensional Fourier transform is applied to convert the data concerned to an image by CPU 8 (with respect to three-dimensional K space data, three-dimensional Fourier transform is applied to convert the data concerned to a three-dimensional image). With respect to the feature of the K space, it has a feature that the influence of echo data in the neighborhood of the center (Kx=Ky=0) (that is, an echo signal measured at the phase encode of zero or a value near to zero) exercises over the entire image. That is, the feature of the echo signal data arranged in the neighborhood of the center of the K space is reflected to the contrast of the whole image.

With respect to the contrast of a local area in an image, the spatial frequency is varied in accordance with the size of a target portion. For example, the contrast of an area of one-pixel size in an image is reflected by the contrast of the echo data of the highest spatial frequency area in the K space (that is the echo signal measured at the maximum phase encode or at a near value). With respect to the contrast of an area of 10-pixel size in an image, the contrast of data of 10 points from a higher spatial frequency in the K space contributes greatly.

Echo signals which are measured at timings different in lapse time from the application time point of the RF pulse 201 (hereinafter referred to as echo time) as in the case of the echo planar method have different contrast information. Therefore, in general, the echo time and the areas of the phase encode gradient magnetic field pulse 204 and the phase blip gradient magnetic field pulse 205 are adjusted by the sequencer 4 so that echo data measured at a time at which it is required to be reflect to the contrast of an image are arranged in the neighborhood of the center of the K space.

FIG. 3(a) shows an aspect of phase rotation occurring in the echo signal after the RF pulse 201 is applied. In MRI, the phase occurring in the echo signal is proportional to the echo time. The phase rotation occurring in the echo signal is likewise proportional to the echo time due to the effect of non-uniformity of magnetic field and the difference in magnetic susceptibility. 301-1, 301-2 and 301-3 represent different phase variations (gradients) of an echo signal after an RF pulse is applied. In general, the non-uniformity of magnetic field and the magnetic susceptibility as described above vary spatially locally, and thus image data varies in phase every position. In the case of the echo planar method, the phase value varies every echo signal in the echo signal group 209 due to the phase variation as described above.

Furthermore, the peak value of the echo signal obtained in the MRI apparatus behaves like a curved line 302 of FIG. 3(b) after the RF pulse 201 is applied. This contains signal attenuation caused by an effect that the phase of spins in the rotational plane which is uniform just after the RF pulse 201 is applied is dispersed with time lapse and thus the echo signal is reduced, and an effect that spins excited by the RF pulse 201 are subjected to transverse relaxation that is, $T_2$ relaxation). Accordingly, the difference in peak value which is dependent on the echo time occurs in the echo signal group 209 measured by the echo planar method.

Next, the principle of the susceptibility-emphasized imaging will be briefly described. A phase difference occurs in spins due to the difference of magnetic susceptibility, and this phase difference is larger as the echo time is longer. When tissues different in magnetic susceptibility are mixed in one-pixel of an image, cancel of NMR signals occurs between the tissues in the pixel concerned due to the phase difference, so that the signal intensity of the pixel concerned is reduced (so-called partial volume effect). An image which is emphasized with a susceptibility effect by using the partial volume effect is a susceptibility-emphasized image. In order to enhance the susceptibility effect, it is preferable to set such a long echo time that the phase difference of spins are as large as possible. As an example, an echo signal at a time point when about 70 ms elapses is required. Therefore, in the conventional susceptibility-emphasized imaging, the repeat time (TR) of the sequence cannot be set to be short and thus the imaging time is long.

Therefore, the susceptibility-emphasized image using the echo planar method described above is considered. However, when they are merely combined, information of echo signals of different echo times is mixed with the phase variation of image data. Therefore, the emphasized effect based on magnetic susceptibility is dispersed to the overall image, and thus weakened, and thus there cannot be obtained any image in which the area of interest on the image is subjected to optimal susceptibility-emphasizing.

The MRI apparatus of this invention solves this problem, and embodiments of the MRI apparatus according to this invention will be described.

First Embodiment

A first embodiment of the MRI apparatus and the MRI method according to the present invention will be described. According to this embodiment, the measuring order of plural echo signals is controlled in accordance with the size of a desired area of interest of an examinee. That is, the measuring order of plural echo signals is controlled in accordance with the size of an area of interest on an image so that an echo signal corresponding to the size of the area of interest concerned is measured at an echo time to which a desired susceptibility effect is reflected. In order to control the measuring order of plural echo signals, the application order of the phase encode gradient magnetic field, that is, the position at which echo data is arranged on the K space is controlled. Specifically, a target frequency in the K space is determined in accordance with the size of the area of interest, and the measuring order of plural echo signals is controlled so that the echo signals corresponding to the target frequency are measured at or in the neighborhood of a target echo time set as an echo time for which a desired susceptibility effect is reflected.

This embodiment will be described with reference to FIGS. 4 and 5. FIG. 4 is a flowchart showing an example of an overall imaging processing flow according to this embodiment, and FIG. 5 is a flowchart showing, particularly, an example of a detailed processing flow of a processing part according to this embodiment in the processing flow of FIG. 4.

First, an example of the overall imaging processing flow will be described with reference to the flowchart of FIG. 4. This processing flow is stored as a program in an external storage device, and CPU 8 or the sequencer 4 reads the program into the memory to execute the program, thereby performing the processing flow.

In step 401, a site to be imaged is selected as in the case of normal imaging. An operator selects an imaging target site through an imaging target site selecting GUI displayed on the display 20, for example. This step 401 may be omitted.

In step 402, parameters of the imaging sequence are set. As in the case of the step 401, the operator sets imaging sequence parameters through a parameter setting GUI displayed on the display 20.

In step 403, it is determined on the basis of the parameters set in step 402 whether the imaging sequence is the susceptibility-emphasized imaging or not. For example, when the parameter setting GUI has a choice for the susceptibility-emphasized imaging and the operator selects the choice concerned, it may be determined that the susceptibility-emphasized imaging is selected. Furthermore, when the gradient echo type multi-shot echo planar method is selected and actual TE (echo time of phase encode zero) is set to along value, it may be determined that the susceptibility-emphasized imaging is selected. This determination is performed by CPU 8.

In step 404, when the susceptibility-emphasized imaging is determined, CPU 8 sets the parameters required for the susceptibility-emphasized imaging. The details of this step 404 will be described later.

In step 405, the imaging sequence is executed. On the basis of the parameters set in step 402, in the case of the susceptibility-emphasized imaging, the sequencer 4 also executes the imaging sequence on the basis of the parameters for the susceptibility-emphasized imaging which are set in step 404, and the imaging is executed, thereby controlling the measurement of the echo signal. The details in the case of the susceptibility-emphasized imaging will be described later. CPU 8 writes the data of each measured echo signal into the memory corresponding to the K space of CPU 8. That is, CPU 8 disposes the measured echo data into the K space.

In step 406, an image is reconstructed by using the K space data obtained in step 405. Specifically, CPU 8 executes Fourier transform on the K space data obtained in step 405 to reconstruct the image. Specifically, with respect to two-dimensional K space data, CPU 8 applies two-dimensional Fourier transform to convert the data concerned to a two-dimensional image. With respect to three-dimensional K space data, CPU 8 applies three-dimensional Fourier transform to convert the data concerned to three-dimensional image.

The foregoing description relates to an example of the overall imaging processing flow.

Next, setting of parameters required for the susceptibility-emphasized imaging of the step 404 will be described with reference to FIG. 5. FIG. 5 is a flowchart showing an example of the processing flow of the parameter setting required for the susceptibility-emphasized imaging.

In step 501, the size of an area of interest on an image (target size) is set. The setting of the target size can be performed as follows.

According to a first method, CPU 8 sets the target size on the basis of information which an operator inputs through the operating system 25. Specifically, a pixel size (number of pixels) of an area of interest input by the operator is set as the target size. Or, the actual size (mm) of the area of interest input by the operator may be set as the target size. For example, as in the case of the MR angiography, when the area of interest is a blood vessel, the operator can set the target size by inputting the diameter of a target blood vessel. Or, CPU 8 may determine the pixel size or the actual size of the area of interest on the basis of input information of a figure (diagram) surrounding an area of interest which is drawn on an image by the operator, thereby setting the target size. An example of setting GUI of the target size will be described later.

According to a second method, the target size may be stored in an external storage device such as the magnetic disk 18 every imaging target size in advance, and CPU 8 may read out stored data in accordance with a specified imaging target site to set the target size. For example, the size of each site such as the diameter (Radius) of a blood vessel is little dependent on patient individual variation, and thus the target size of each imaging target site can be uniquely set irrespective of patients. The details will be described with reference to a second embodiment described later.

In step 502, the target frequency (Target Frequency) is set. CPU 8 sets the position on the K space at which the echo data corresponding to the target size set in step 501 should be arranged, that is, the target frequency.

As an example of the method of setting the target frequency, when the target size is set on the basis of a pixel size (Size), the target frequency is calculated according to the following mathematical expression (expression 1) by using an image matrix (Matrix) on the basis of the input information.

$$\text{Target Frequency} = \pm(\text{Matrix}/2 - (\text{Size} - 1)) \quad \text{(expression 1)}$$

Or, when the target size is set on the basis of the actual size (mm) (Radius) of the area of interest, CPU 8 calculates the target frequency according to the following calculation from a field of view (FOV) for imaging and an imaging matrix (Matrix).

$$\text{Target Frequency} = \pm(\text{Matrix}/2 - (\text{Radius}/(\text{FOV}/\text{Matrix}) - 1)) \quad \text{(expression 2)}$$

As described above, the target frequency which is settled in accordance with the target size is set to any spatial frequency from the original point to the maximum spatial frequency in the Ky direction (phase encode direction) of the K space.

In step 503, the target echo time is set. The target echo time is an echo time required to enable a desired magnetic susceptibility to be reflected to the phase information of the echo signal. The target echo time may be set through the operating system 25 by the operator. Alternatively, the target echo time of each imaging target site may be pre-stored in the external storage device such as the magnetic disk 18 in consideration of the magnetic susceptibility of each imaging target site, and CPU 8 may read out the stored data in accordance with the indicated imaging target site to set the target echo time. For example, the target echo signal is set to 70 msec as an example as described above.

This step may be executed before the setting of the target size of the step 501 described above. In short, the target frequency and the target echo time may be set before the next step 504 is started.

In step 504, the measuring order of the respective echo signals is set. CPU 8 sets the measuring order of the respective echo signals so that the echo signal of the target frequency set in step 502 is measured at the target echo time set in step 503. CPU 8 adjusts the application amount (the area of the pulse waveform) of the phase encode gradient magnetic field pulse 204 and the phase blip gradient magnetic field pulse 205 so that imaging is executed in the set measuring order of the respective echo signals.

As described above, in order to enable the echo signal of the target frequency to be measured at the target echo time, it is necessary to change the measuring order of the respective echo signals. At this time, it is preferable that echo data measured at a late echo time are arranged at a higher frequency side than the target frequency on the K space. As described above, by arranging the data of the respective echo signals in the K space, the phase variation near to the target echo time can be reflected to the structure within the size of the area of interest.

The foregoing description relates to an example of the processing flow of the parameter setting required for susceptibility-emphasized imaging.

Next, a case where the imaging executed in step 405 is the susceptibility-emphasized imaging based on the respective parameters required for the susceptibility-emphasized imaging which are set as described above will be described in detail.

In step 405 (susceptibility-emphasized imaging), the susceptibility-emphasized imaging is executed, and an echo signal to which the susceptibility effect is reflected is measured. The sequence 4 controls the measurement of the respective echo signals so that the measuring order of the echo signals is set to the measuring order set in step 504. That is the sequencer 4 executes the imaging by using the gradient echo type multi-shot echo planar method having the areas of the phase encode gradient magnetic field pulse 204 and the phase blip gradient magnetic field pulse 205 which are adjusted in step 504, and control the measurement of the respective echo signals.

FIG. 6 schematically shows the K space in which the measured respective echo data are disposed. In the diagram of the K space data coloring is executed so that an area corresponding to echo signals measured when the echo time is short is whitened and the area is darkened with black as the echo time is longer. The schematic diagram of the K space data is likewise shown below.

FIG. 6 schematically shows the K space data obtained by using the gradient echo type multi-shot echo planar method described with reference to FIG. 2, and it shows that twelve echo signals are obtained by one shot of RF pulse 201, and echo signals at the positive side in the Ky direction and echo signals at the negative side in the Ky direction are measured by repeating the sequence twice.

In an example of FIG. 6(a), the size of an area of interest is set to 6 pixels, so that the target frequency 601 (suffixes 1, 2 of FIG. 6 represent a first sequence and a second sequence. same as above) is set to a spatial frequency of Ky=±6, and FIG. 6(a) shows K space data obtained when an echo for which the target echo time is the longest echo time (that is, echo number=twelfth) is set. Accordingly, in FIG. 6(a), with respect to the measuring order of the echo signal corresponding to the position in the Ky direction, at the positive side, the echo signals are obtained in the first sequence as follows:

echo number (Ky)=1(1), 2(2), 3(3), 8(4), 10(5), 12(6), 11(7), 9(8), 7(9), 6(10), 5(11), 4(12)

At the negative side, the echo signals are obtained in the second sequence as follows:

echo number (Ky)=1(−1), 2(−2), 3(−3), 8(−4), 10(−5), 12(−6), 11(−7), 9(−8), 7(−9), 6(−10), 5(−11), 4(−12)

At the position of Ky=±6, the echo data of the echo number 12 measured at the target echo time are disposed. In the surrounding spatial frequency area, echo data of echo numbers 11 and 10 measured at an echo time near to the target echo time are disposed, and echo data are successively disposed in the order that the echo time of the echo data is farther away from the target echo time. In this measuring order, the echo data for which the echo time is longest is disposed at the position of Ky=±6, and thus the phase value of the area of about 6 pixels within the image reflects the phase value of the target echo time.

FIG. 6(b) is a schematic diagram showing K space data obtained in another order. The size of an area of interest is set to one pixel, and the target frequency 602 is set to the maximum spatial frequency of the K space. FIG. 6(b) shows K space data obtained when an echo for which the target echo time is the longest echo time (that is, echo number=twelfth) is set. Accordingly, an echo signal having a short echo time is disposed in the neighborhood of Ky=0 of the K space, and an echo signal is disposed at a higher spatial frequency side of the K space as the echo time thereof is longer. Specifically, in the case of FIG. 6(b), with respect to the measuring order of the echo signal corresponding to the position in the Ky direction, at the positive side, the echo signals are obtained in the first sequence as follows:

echo number (Ky)=1(1), 2(2), 3(3), 4(4), 5(5), 6(6), 7(7), 8(8), 9(9), 10(10), 11(11), 12(12)

At the negative side, the echo signals are obtained in the second sequence as follows:

echo number (Ky)=1(−1), 2(−2), 3(−3), 4(−4), 5(−5), 6(−6), 7(−7), 8(−8), 9(−9), 10(−10), 11(−11), 12(−12)

That is, at both the positive and negative sides of the K space, the absolute value of Ky and the echo number are coincident with each other. According to this measuring order, the echo data for which the echo time is longest is disposed at the position of the highest spatial frequency in the K space, and thus the phase value of the area of about 1 pixel within the image reflects the phase value of the target echo time. As described above, the data disposed at the high spatial frequency side of the K space has meaning and feature which are inherent to this embodiment. Therefore, the feature of the data is completely different from that of the K space data of the conventional centric ordering.

As is apparent from the above two examples, the target frequency can be set to any spatial frequency from the origin to the maximum spatial frequency in the phase encode direction (Ky) of the K space. The sequencer 4 controls application of the phase encode gradient magnetic field and the phase blip gradient magnetic field to control the measuring order of plural echo signals.

The foregoing description relates to the case where the step 405 described above corresponds to the susceptibility-emphasized imaging. According to the susceptibility-emphasized imaging using the gradient echo type multi-shot echo planar method based on the processing flow, an image in which a desired area of interest having a target size is optimally susceptibility-emphasized can be obtained.

Next, an example of target size setting GUI described with reference to the step 501 will be described with reference to FIG. 7. FIG. 7 shows GUI 701 displayed on the display 20 when the susceptibility-emphasized imaging is determined, and 702 represents an input unit for inputting the target size. The target size input through GUI 701 can be applied to any one of the two calculation expressions (expression 1, expression 2).

With respect to the target size, a case of inputting the absolute size in units of mm and a case of converting the absolute size to the number of pixels of an image and inputting it may be selected, for example. Therefore, they are switchable by using a unit setting button or the like as shown in FIG. 703. When an OK button 704 is clicked by a mouse after the input, the input target size is set.

As described above, the operator can set the target size, whereby the contrast of the susceptibility-emphasized image can be matched with a desired site structure.

As described above, according to the MRI apparatus and the MRI method of this embodiment, in the susceptibility-emphasized imaging using the gradient echo type multi-shot echo planar method, the measuring order of the respective echo signals is controlled so that the phase of the target echo time is most reflected to the echo signals of the target frequency corresponding to the target size (that is, the application of the phase encode is controlled to control the arrangement order on the K space of the respective echo data), thereby obtaining an image in which a desired area of interest having the target size can be optimally susceptibility-emphasized. As a result, the contrast concerning the susceptibility-emphasizing can be enhanced in the susceptibility-emphasized image obtained by the susceptibility-emphasized imaging of this embodiment.

Second Embodiment

A second embodiment of the MRI apparatus and the MRI method according to the present invention will be described. In this embodiment, the first embodiment described above is expanded to three-dimensional imaging. That is, the measuring order of plural echo signals is controlled so that echo signals corresponding to a spatial frequency area located at the same distance from the origin of a Ky-Kz space are measured in the same echo time range in a three-dimensional space k space having a phase encode direction (ky) and a slice encode (Kz) direction. Specifically, the spatial frequency area located in the same distance range from the origin of the Ky-Kz space is selected as a target frequency, and the measuring order of plural echo signals is controlled so that echo signals corresponding to the selected spatial frequency area are measured at or in the neighborhood of the target echo time. The target frequency can be set to any spatial frequency located at a distance range from zero to the maximum space frequency from the origin of the Ky-Kz space. Only different points from the first embodiment described above will be described, and description of the same points is omitted.

First, in order to clarify the feature of this embodiment, a conventional three-dimensional gradient echo type multi-shot echo planar method will be described with reference to FIG. 8. The difference between the three-dimensional sequence shown in FIG. 8(*a*) and the two-dimensional sequencer shown in FIG. 2(*a*) resides in that a slice encode gradient magnetic field pulse 801 is subsequent to the slice selecting gradient magnetic field pulse 201. The other is the same as the sequence of FIG. 2(*a*), and thus the description thereof is omitted.

FIG. 8(*b*) shows an example in which echo data measured by using the three-dimensional sequence shown in FIG. 8(*b*) are arranged in the three-dimensional K space. FIG. 8(*b*) shows the Ky-Kz space (802) out of the three-dimensional K space. In this case, with respect to the Ky direction, echo data for which the echo time is short are arranged in the neighborhood of Ky=0, and echo data for which the echo time is long are arranged at a high spatial frequency side of the K space (that is, in the areas 803 to 808 of the K space, the echo time is successively increased in the order of 803, 804, 805, ..., 808).

Paying attention to the Kz direction, the slice encode gradient magnetic field pulse 801 is applied after the slice selecting gradient magnetic field pulse 202, and thus no slice encode gradient magnetic field pulse exists when the echo signal group 209 is measured. Therefore, in the Kz direction, echo signals of the same echo time are measured, and there is no difference in echo time between the echo signals. Accordingly, with respect to the phase of the high spatial frequency area which is important for the susceptibility-emphasized imaging, plural echo signals which are measured at different echo times are mixed in all the spatial frequency values in the Kz direction (that is, on a line parallel to the Ky axis direction at any Kz value). Therefore, the emphasized effect based on magnetic susceptibility is dispersed and reduced in the z direction in the image, so that no optimally susceptibility-emphasized image can be obtained.

Next, FIG. 9(*a*) shows the three-dimensional sequence of this embodiment. The difference from the conventional three-dimensional sequence shown in FIG. 8(*a*) resides in that a slice blip gradient magnetic field pulse 902 is applied after the slice encode gradient magnetic field pulse 901. At this time the sequencer 4 controls application of the phase encode gradient magnetic field pulse 204, the phase blip gradient magnetic field pulse 205, the slice encode gradient magnetic field pulse 901 and the slice blip gradient magnetic field pulse 902 so that echo data measured at the same time or in the same echo time range in the spatial frequency area located at the same distance or in the same distance range from the origin in the Ky-Kz space, that is, the echo data are arranged concentrically. As shown in FIG. 9(*b*), the control of application of the respective gradient magnetic field pulses to arrange data concentrically will be described later.

FIG. 9(*b*) shows an example of K space data obtained by executing the three-dimensional sequence shown in FIG. 9(*a*). FIG. 9(*b*) shows the Ky-Kz space (903) out of the three-dimensional K space. As shown in FIG. 9(*b*), the effect of arranging the echo data measured at the same echo time or in the same echo time range in the spatial frequency area located at the same distance or in the same distance range from the origin of the K space resides in that a three-dimensional image in which the contrast caused by the susceptibility effect is enhanced in a desired area can be obtained. That is, in the three-dimensional image reconstructed from the 3-dimensional K space data described above, the phase variation caused by a desired susceptibility effect can be added to the pixel size of a desired three-dimensional area of interest isotropically and equally in each of the three-dimensional axial directions, and thus a three-dimensional susceptibility-emphasized image in which the contrast caused by the susceptibility effect of a desired area is enhanced can be obtained.

Furthermore, according to this embodiment, in the three-dimensional measurement, the measuring order of respective echo signals is controlled so that echo signals of the target frequency corresponding to the target size described with reference to the first embodiment are measured at the target echo time. Therefore, the sequencer 4 controls application of the phase encode gradient magnetic field pulse 204, the phase blip gradient magnetic field pulse 205, the slice encode gradient magnetic field pulse 901 and the slice blip gradient magnetic field pulse 902 so that the measuring order of the respective echo signals as described above is established.

FIG. 9(b) schematically shows the K space in which respective echo data measured by setting a target frequency 907 are arranged. That is, it shows a case where an area 907 out of the areas 904 to 909 of the K space is set as the target frequency 907. The processing flow of FIGS. 4 and 5 described with reference to the first embodiment is applied to the three-dimensional measurement by using the sequence shown in FIG. 9(a), thereby obtaining the three-dimensional K space data as described above.

In step 401, an imaging target site is set (may be omitted), in step 402, imaging sequence parameters of the three-dimensional echo planar method shown in FIG. 9(a) are set, in step 403, susceptibility-emphasized imaging using the three-dimensional echo planar method shown in FIG. 9(a) is determined, in step 404, parameters required for the susceptibility-emphasized imaging using the three-dimensional echo planar method shown in FIG. 9(a) are set, and in step 405, the K space data shown in FIG. 9(b) are obtained by the three-dimensional susceptibility-emphasized imaging.

In step 404, as in the case of the first embodiment, in step 501, the target size is set, in step 502, the target frequency 907 is set, in step 503, a target echo time the longest echo time in the case of FIG. 9(b)) is set, and in step 504, the measuring order of respective echo signals is set so that the echo signals of the target frequency 907 are measured at the target echo time. The application amounts of the phase encode gradient magnetic field pulse 204 and the phase blip gradient magnetic field pulse 205, and the slice encode gradient magnetic field pulse 901 and the slice blip gradient magnetic field pulse 902 are set in accordance with the measuring order.

The processing contents of the respective steps are the same as the respective processing shown in FIGS. 4 and 5 described with reference to the first embodiment, and the detailed description thereof is omitted.

The result of these series of processing is the K space data of FIG. 9(b). As described above, the target frequency which is determined in accordance with the target size is set to any spatial frequency which is located at a distance in the range from zero to the maximum spatial frequency from the origin of the Ky-Kz space.

In the K space data shown in FIG. 9(b) obtained as described above, echo data of a short echo time are arranged in the neighborhood of Ky=0, echo data measured at the target echo time (in this case, the longest echo time) is arranged at the target frequency 907, and at the outside of the target frequency 907, echo data of a longer echo time are arranged to be nearer to the target frequency 907 side (that is, the echo time is successively longer in the order of 904, 905, 906, 909, 908, 907 of the areas 904 to 909 of the K space).

As described above, the measuring order of the respective echo signals is controlled so that the echo signals of the target frequency are measured at the target echo time, whereby the same effect as the first embodiment can be obtained in the three-dimensional susceptibility-emphasized image. That is, the echo signals of the target frequency are measured at the target echo time, and also the echo data thereof are arranged in an area located at an equidistance from the origin of the three-dimensional K. Therefore, the phase variation is most strongly added to the image data of the three-dimensional area of interest having the pixel size corresponding to the target frequency isotropically and equally in each of the three-dimensional axial directions. As a result, the three-dimensional image in which the area of interest having the pixel size corresponding to the target frequency is most strongly susceptibility-emphasized can be obtained.

Next, an example of enhancing the efficiency of the data arrangement of each divisional area in the Ky-Kz plane will be described. In the three-dimensional sequence shown in FIG. 9(a), the application amounts of the slice blip gradient magnetic field 902 and the phase blip gradient magnetic field pulse 205 are constant, and thus the K space is divided so that the widths in the radial direction of respective divisional areas are equal to one another. As a result, the areas of the respective divisional areas are greatly different from one another. This means that echo data is arranged in each divisional area every echo time and thus the amount of echo signals required to be filled in each divisional area is different.

Therefore, with respect to the width in the radial direction of the spatial frequency area which is located in the same distance range from the origin of the Ky-Kz space, the width at the high spatial frequency side is set to be smaller than that at the low spatial frequency side. Specifically, a control method of controlling the application amount of at least one of the slice blip gradient magnetic field pulse 902 and the phase blip gradient magnetic gradient magnetic field pulse 205 to equally arrange data in respective divisional areas within the Ky-Kz plane will be described with reference to FIG. 10.

As shown in FIG. 10(b), the K space is divided so that the areas 1007 to 1012 of the respective spatial frequencies of the Ky-Kz space 903 have the same area, that is, the width in the radial direction of each divisional area is narrowed as the spatial frequency is shifted to a higher spatial frequency side (that is, the width in the radial direction of the divisional area is set to be smaller at the higher spatial frequency side than that at the lower frequency spatial frequency side, whereby the amount of echo signals required to be filled in each divisional area is equal, and thus the efficiency of the data arrangement is enhanced. With respect to a target frequency 1005, it is the same as 905 of FIG. 9(b). FIG. 10(a) shows an example of a three-dimensional sequence to obtain the K space data as described above. As shown in FIG. 10(b), the application amount of at least one of the slice blip gradient magnetic field pulse 1002 after the slice gradient magnetic field pulse 1003 and the phase blip gradient magnetic field pulse 1004 after the phase encode gradient magnetic field 1001 in the three-dimensional sequence is reduced every blip, that is, as the echo number incremented in connection with the reduction of the width in the radial direction of each divisional area of the K space as the frequency area is shifted to the high spatial frequency side.

Finally, the control of the application of the respective gradient magnetic field pulses so that the echo data which are measured at the same echo time or in the same echo time range are arranged in the spatial frequency area located at the same distance or in the same distance range from the origin in the Ky-Kz space, that is, the data are arranged concentrically will be described hereunder with reference to FIG. 11.

FIG. 11 schematically shows an example of a method of obtaining K space data based on three-dimensional measurement according to this embodiment. In FIG. 11, a quarter of the Ky-Ky space is shown for simplification. FIG. 11 shows a case where the three-dimensional sequence shown in FIG. 9(a) is used, five echo signals 209 are measured by each one-shot (that is, five spatial frequency areas are obtained), and twelve shots of 1101-1 to 1101-12 are required to fill the quarter of Ky-Kz. Circles of FIG. 11 represent points which represent the positions of Ky-Kz of measured echo signals, and arrows represent echo signal measuring directions.

Here, when s represents a shot number (1≤s≤S), e represents an echo train number (1≤e≤E), and the size of the K space is Matrix, as a sequence calculation, an angle θ(s) for measuring echo signals every shot is calculated as follows.

$$\theta(s) = 2\pi/S \times s \quad \text{(expression 3)}$$

Subsequently, the K space pitch ΔK between echo trains is calculated as follows.

$$\Delta K = \text{Matrix}/2/E \quad \text{(expression 4)}$$

From these two values, the area of the blip gradient magnetic field to be applied every shot is calculated on the basis of the steps of the K space in the Ky, Kz directions at each shot:

$$\Delta Ky(s) = \Delta K \times \cos(\theta(s))$$

$$\Delta Kz(s) = \Delta K \times \sin(\theta(s)) \quad \text{(expression 5)}$$

The Ky-Kz space can be also filled under this state. However, when the number of echo signals is small, a displacement occurs in an echo-signal measuring area in the K space, and thus it is preferable that a start point to start measurement of an echo signal is shifted in the K space every shot. For example, in FIG. 11, the start point is shifted outwardly in the radial direction every three other shots (in FIG. 11, the displacement amount is represented by shading of the circles).

As described above, the following calculation may be executed to measure echo signals. First, a shift amount as a reference of the start point of the measurement at each shot is calculated. At this time, when the shift amount is varied every N shots, $$\Delta S(s) = \Delta K/N \times (s \bmod N) \quad \text{(expression 6)}$$

Here, A mod B represents the remainder when A is divided by B. On the basis of this start point ΔS(s), the shift position Skx(s), Sky(s) of the K space at each shot is calculated by using the rotational angle θ(s) of each shot:

$$Skx(s) = \Delta S(s) \times \cos(\theta(s))$$

$$Sky(s) = \Delta S(s) \times \sin(\theta(s)) \quad \text{(expression 7)}$$

The output of the phase encode gradient magnetic field pulse (204, 1003) and the output of the slice encode gradient magnetic field pulse (901, 1001) are changed on the basis of these values.

The foregoing description relates to the control of the application of each gradient magnetic field pulse to arrange data concentrically in the Ky-Kz space.

As described above, according to the MRI apparatus and the MRI method of this embodiment, the effect of the first embodiment is also obtained in the three-dimensional image. That is, the measuring order of the respective echo signals and the arrangement on the K space of the data of the respective echo signals are controlled (that is, application of each encode gradient magnetic field and each blip gradient magnetic field is controlled) in the three-dimensional echo planar method so that the phase of the target echo time is most reflected to the echo signals of the target frequency corresponding to the target size. Therefore, a three-dimensional image in which a desired three-dimensional area of interest having a target size is optimally susceptibility-emphasized can be obtained.

Third Embodiment

Next, a third embodiment of the MRI apparatus and the MRI method according to this invention will be described. According to this embodiment, the K space is not divided into two parts at the positive and negative sides in the Ky direction of the K space to perform measurements at each side, but echo signals at both the positive and negative sides are measured concurrently within one repeat of the sequence. Specifically, plural echo signals are measured while the polarity of the phase blip gradient magnetic field in the case of two-dimensional imaging or the polarity of at least one blip gradient magnetic field of the phase blip gradient magnetic field and the slice blip gradient magnetic field in the case of three-dimensional imaging is alternately reversed. Only the different point from the first embodiment described above will be described, and the description of the same point is omitted.

FIG. 12(a) shows an example of the sequence used in this embodiment. The difference from FIG. 2(a) resides in the application amount of the phase encode gradient magnetic field pulse 1201 for determining the measurement start point in the Ky direction at each shot (between 210) and the application method of the phase blip gradient magnetic field pulse group 1202 for determining the measuring order in the Ky direction. In the example of FIG. 12(a), echo signals are measured while the polarity of the phase blip gradient magnetic field pulse is alternately reversed every one-echo by the sequencer 4. However, the application amount of each phase blip gradient magnetic field pulse is controlled because echo signals of the set target frequency are measured in the set measuring order, that is, the echo signals of the set target frequency are measured at the target echo time. In the example of FIG. 12(a), the echo signals corresponding to the K space high band are measured prior to the echo signals of the target frequency, the application amount of the phase blip 1220 is increased because of measurement of the echo signal corresponding to the opposite-side high band of the K space to the just-before echo signal, the next blips 1221-1, 1222-1 are echo signal pulses of the target frequency set in the middle band of the K space, and the application amount is reduced. The sequencer 4 controls the sequence as described above and repeats this sequence once or plural times to obtain the K space data. Particularly, when the whole K space is obtained by one sequence, necessary K space data are obtained by irradiation of one RF pulse 201, and thus the measurement can be performed in an extremely short time (several tens msec).

FIG. 12(b) shows an example of the K space data obtained by using the sequence as described above. FIG. 12(b) shows K space data obtained when the divisional areas 1206 and 1207 are set as target frequency areas. The sequencer 4 controls the phase encode gradient magnetic field pulse 1201 and the phase blip gradient magnetic field pulse 1202 so that the measurement is started from the echo signal corresponding to the center area 1203 of the K space and the echo signals corresponding to the target frequency areas and the high spatial frequency area are successively measured in the order of 1204, 1205, 1206 and 1207. In this case, the echo time is longer in the order of 1203, 1204, 1205, 1206 and 1207.

As described above, the echo data which are measured substantially at the same time are arranged in the same spatial frequency area of the K space (however, signs are different) by concurrently measuring the echo signals at both the positive and negative sides in the Ky direction within one repeat of the sequence without dividing the K space into two parts at the positive and negative sides in the Ky direction to perform the measurement at both the sides. Accordingly, an image in which an area of interest having the size corresponding to the target frequency is susceptibility-emphasized can be obtained.

FIG. 12(c) shows a case where the measuring order of the echo signals is replaced between the positive and negative sides in the Ky direction, and shows K space data obtained when divisional areas 1211 and 1212 are set as target frequency areas. The echo data are arranged in the order of 1208, 1209, 1210, 1211, 1212 (the echo time for the measurement of the echo signals arranged in the order of 1208 to 1212 is increased in the order of 1208, 1209, 1210, 1211, 1212 as in the case of FIG. 12(b)). Even when the arrangement as described above is adopted, the shape of the K space is substantially equal, and thus an obtained image has the same result as shown in FIG. 12(b).

Furthermore, the sequences as shown in FIG. 12(b) and FIG. 12(c) can be combined with each other. For example, it can be selected every shot which one of the orders is used. In this case, the order may be selected so that the echo data of a target echo time are arranged in a target positive/negative spatial frequency area.

The other points are the same as the first embodiment described above, and thus the description thereof is omitted.

As described above, according to the MRI apparatus and the MRI method of this embodiment, in the susceptibility-emphasized imaging using the gradient echo type echo planar method, substantially the same effect as the first embodiment can be obtained by measuring both the echo signals at both the positive and negative sides in the Ky direction within one repeat of the sequence. Particularly, when all the K space data are obtained by one sequence, the same effect as the first embodiment can be obtained in a shorter time.

Fourth Embodiment

Next, a fourth embodiment of the MRI apparatus and the MRI method according to the present invention will be described. In this embodiment, the optimum target frequency is determined in accordance with the imaging target site. The different point from the first embodiment resides in that the imaging target site is selected and also the target size setting of the step 501 and the target frequency setting of the step 502 are executed on the basis of information pre-stored every imaging target site. Only the different point from the first embodiment will be described, and the description of the same points is omitted. This embodiment may be combined with each of the other embodiments.

First, the selection of the imaging target site will be described. This step may be executed in the step 401, or may be separately provided before the step 501 and executed. The processing flow of this embodiment is identical to the processing flow shown in FIGS. 4 and 5 in the first embodiment, however, the content of the processing is different. An example of the processing flow of this embodiment when an imaging target site selecting step 500 is separately provided in the processing flow of FIG. 5 will be described hereunder. However, the processing content of this step may be executed in the step 401 with omitting the step 500.

In step 500, the imaging target site is selected. The operator selects a desired imaging target site on a selecting GUI of the imaging target site. FIG. 13(a) shows an imaging target site selecting window 1301 as an example of the selecting GUI of the imaging target site. Plural imaging target sites 1302 are displayed in a list style together with radio frequency buttons. FIG. 13(a) shows an example in which head portions A and B, abdominal parts A, B and four limbs are displayed as options. The operator selects the radio frequency button of a desired imaging target site from these options. In FIG. 13(a), the head portion A is selected. Finally, the operator clicks the OK button 1303 by the mouse, and CPU 8 sets the option concerned as an imaging target site.

In step 501, the target size is set on the basis of the information pre-stored every imaging target site. In general, the target size of each imaging target site can be statistically determined. For example, as shown in FIG. 13(b), a table 1304 for associating the target site (or the imaging method for the imaging target site) and the target size is prepared in advance, and stored in the external storage device such as the magnetic disk 18. CPU 8 reads out the target size corresponding to the imaging target site set in the step 401 or the step 500 from the table 1304 in step 501 to set the target size.

The example of FIG. 13(b) is a table 1304 in which rough minimum size and maximum size of an importable tissue targeted in the susceptibility-emphasized imaging are stored every imaging target site. A merit that the minimum size and the maximum size are used resides in that the target frequency can be calculated for each size according to the (expression 2).

In step 502, the target frequency is set on the basis of the target size read out from the table in step 501. When the minimum size ($Radius_{min}$) and the maximum size ($Radius_{max}$) of each imaging target site of FIG. 13(b) are used, the maximum Target Frequency$_{max}$ and the minimum Target Frequency$_{min}$ of the target frequency can be calculated as follows:

$$\text{Target Frequency}_{max} = \pm(\text{Matrix}/2 - (\text{Radius}_{min}/(\text{FOV}/\text{Matrix}) - 1)) \quad \text{(expression 8)}$$

$$\text{Target Frequency}_{min} = \pm(\text{Matrix}/2 - (\text{Radius}_{max}/(\text{FOV}/\text{Matrix}) - 1)) \quad \text{(expression 9)}$$

When the susceptibility-emphasized imaging sequence is executed, CPU 8 sets the measuring order of respective echo signals so that echo signals in the range of these two target frequencies (spatial frequencies) are measured at the target echo time or in the neighborhood of the target echo time.

The foregoing description relates to the processing content inherent to this embodiment. The other points are the same as the first embodiment, and thus the description thereof is omitted. Accordingly, by merely selecting the imaging target site, the operator can obtain an image in which the area of interest at the imaging target site is automatically optimally susceptibility-emphasized.

In this embodiment, the minimum target size and the maximum target size are used, this embodiment is not limited to this style. For example, an average target size may be used. In the case of the average target size, only one target frequency corresponding to the value concerned is determined, and the measurement order of respective echo signals is set so that the echo signals of the target frequency are measured at the target echo time.

Furthermore, in this embodiment, the table in which the target size is registered every imaging target site is prepared in advance, and the target size is set by selecting an imaging target site. However, a table in which the target size is registered may be prepared in advance not every imaging target site, but every affection or every tissue name (blood vessel name or the like) so that the target size is set by selecting an affection or tissue name.

As described above, according to the MRI apparatus and the MRI method of this embodiment, in the susceptibility-emphasized imaging using the echo planar method, the target size of each imaging target site or the like is prepared in a table style in advance, and the target size and the target frequency can be automatically set in accordance with the selection of an imaging target site or the like. Therefore, an image in which a desired area of interest having a target size can be optimally susceptibility-emphasized can be easily obtained.

BRIEF DESCRIPTION OF THE DRAWINGS

FIG. 2 are diagrams showing (a) a sequence of a gradient echo type multi-shot type planar method and (b) K space data measured by the sequence.

FIG. 3 is a diagram showing variation of an echo signal based on the echo planar method.

FIG. 9 shows (a) a three-dimensional sequence chart, and (b) K space data measured in the sequence according to a second embodiment.

FIG. 10 shows (a) a three-dimensional sequence chart and (b) K space data measured in the sequence in an example of enhancing the efficiency of the data arrangement of each divisional area in Ky-Kz plane in the second embodiment.

FIG. 11 is a diagram showing the control of application of each gradient magnetic field pulse so that echo data measured at the same echo time are arranged in a spatial frequency area located at the same distance from the origin in the Kz-Ky space.

FIG. 12 shows (a) a two-dimensional sequence chart and (b) K space data measured in the sequence according to a third embodiment.

FIG. 13 shows (a) an imaging target site selecting window, and (b) a table in which a target size of each imaging target site is registered according to a fourth embodiment.

DESCRIPTION OF REFERENCE NUMERALS 1 examinee, 2 magnetostatic field generating system, 3 gradient magnetic field generating system, 4 sequencer, 5 transmission system, 6 reception system, 7 signal processing system, 8 central processing unit (CPU), 9 gradient magnetic field coil, 10 gradient magnetic field power source, 11 radio frequency oscillator, 12 modulator, 13 radio frequency amplifier, 14a radio frequency coil (transmission side), 14b radio frequency coil (reception side), 15 amplifier, 16 orthogonal phase detector, 17 A/D converter, 18 magnetic disk, 19 optical disc, 20 display, 201 RF pulse, 202 slice selecting gradient magnetic field pulse, 203 slice refocus selecting gradient magnetic field pulse, 204 phase encode gradient magnetic field pulse, 205 phase blip gradient magnetic field pulse, 206 frequency dephasing gradient magnetic field pulse, 207 frequency encode gradient magnetic field pulse, 208 data sample window, 209 echo signal FIG. 1
4: SEQUENCER
9: GRADIENT MAGNETIC FIELD COIL
10: GRADIENT MAGNETIC FIELD POWER SUPPLY
11: RADIO FREQUENCY OSCILLATOR
12: MODULATOR
14a, 14b: RADIO FREQUENCY COIL
16: ORTHOGONAL PHASE DETECTOR
18: MAGNETIC DISK
19: OPTICAL DISC
20: DISPLAY
23: TRACK BALL OR MOUSE
24: KEYBOARD
FIGS. 3(a), (b)
エコー時間 : ECHO TIME
FIG. 4
401: SELECT IMAGING TARGET SITE
402: SET IMAGING PARAMETERS
403: SUSCEPTIBILITY-EMPHASIZED IMAGING ?
404: SET SUSCEPTIBILITY-EMPHASIZED PARAMETERS
405: EXECUTE SEQUENCE
406: RECONSTRUCT IMAGE
FIG. 5
501: SET SIZE OF AREA OF INTEREST
502: SET TARGET FREQUENCY
503: SET TARGET ECHO TIME
504: SET ORDER OF OBTAINING ECHO SIGNALS
FIG. 7
ターゲットサイズ : TARGET SIZE
単位 : UNIT
FIG. 13(a)
対象部位 : TARGET SITE
頭部 A: HEAD PORTION A
腹部 A: ABDOMINAL PART A
下肢 : LOWER LIMB
頭部 B: HEAD PORTION B
腹部 B: ABDOMINAL PART B
FIG. 13(b)
部位 : SITE
最小ターゲットサイズ : MINIMUM TARGET SIZE
最大ターゲットサイズ : MAXIMUM TARGET SIZE
頭部 A: HEAD PORTION A
頭部 B: HEAD PORTION B
頚部 A: CERVICAL PART A
頬部 A: CERVICAL PART A
腹部 A: ABDOMINAL PART A

Figure 1:
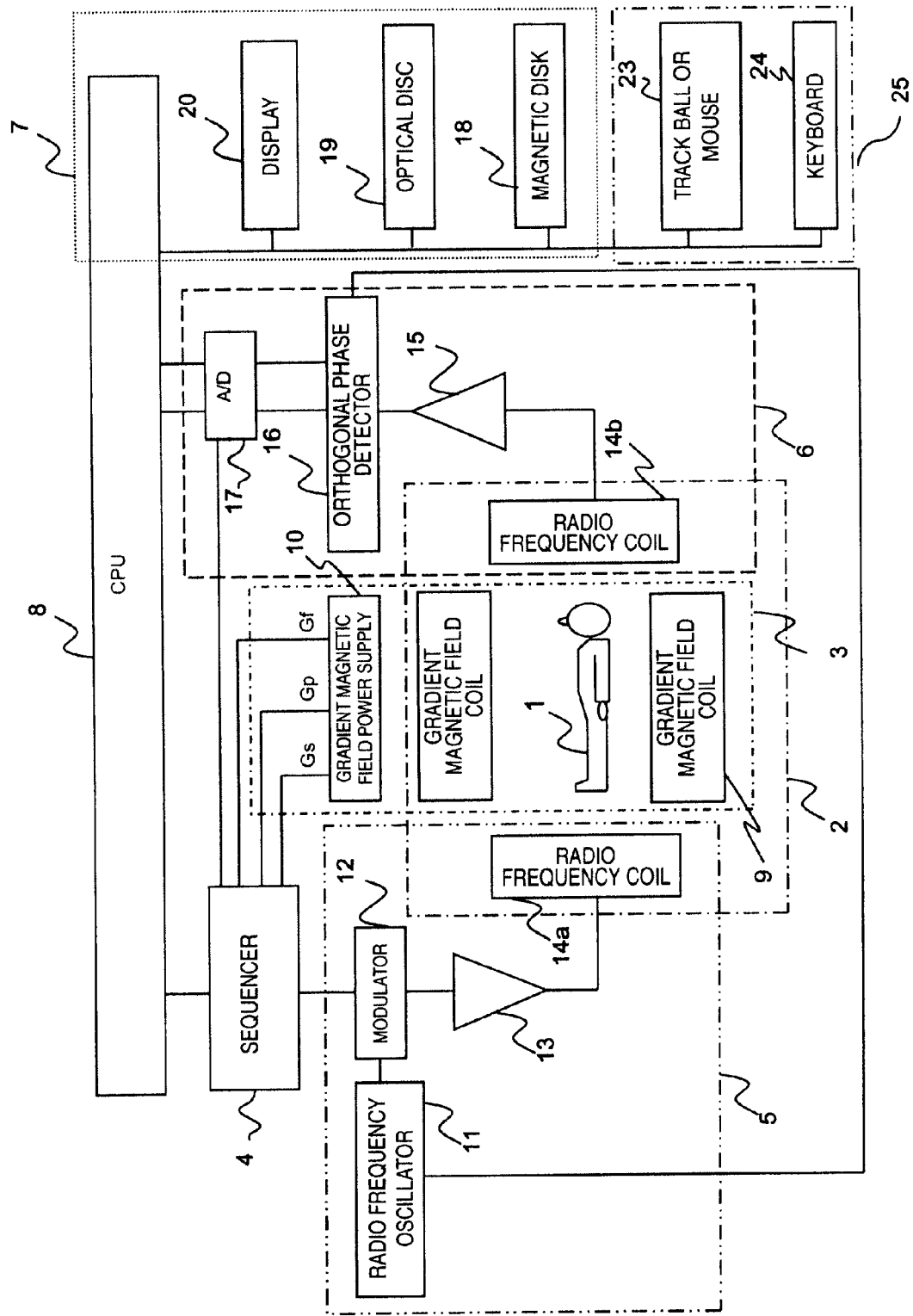
FIG. 1 is a diagram showing the overall construction of an MRI apparatus to which the present invention is applied.
Figure 4:
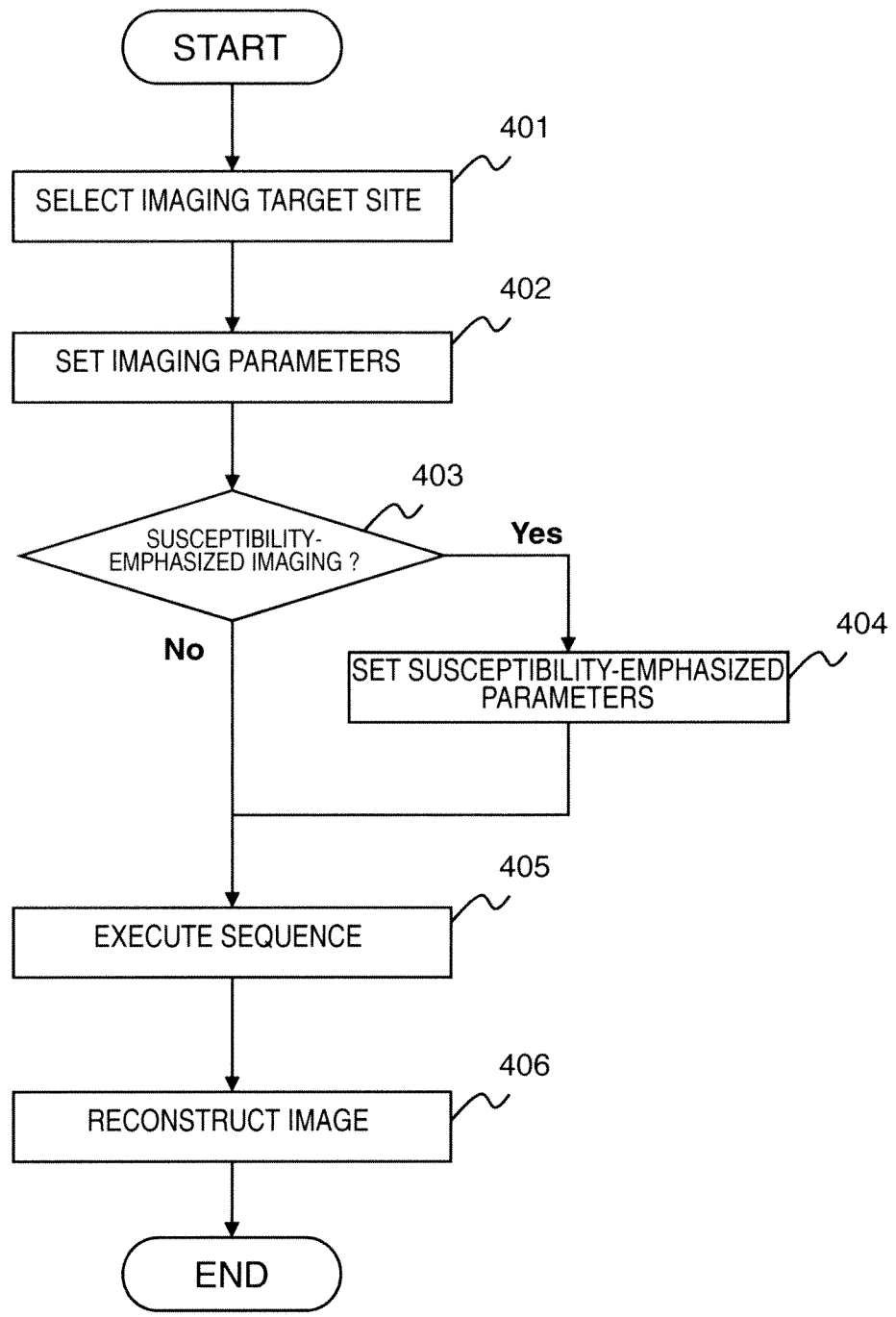
FIG. 4 is a diagram showing the overall imaging processing flow of a first embodiment.
Figure 5:
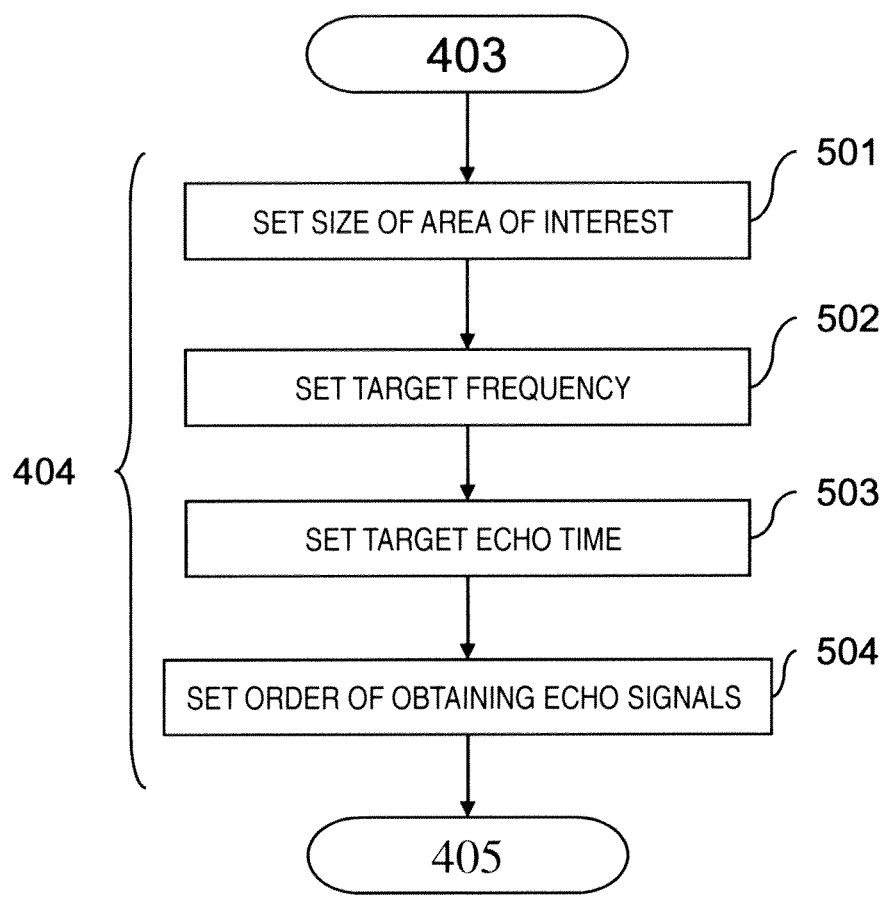
FIG. 5 is a diagram which particularly shows the detailed processing flow of a processing part according to the first embodiment in the processing flow of FIG. 4.
Figure 6:
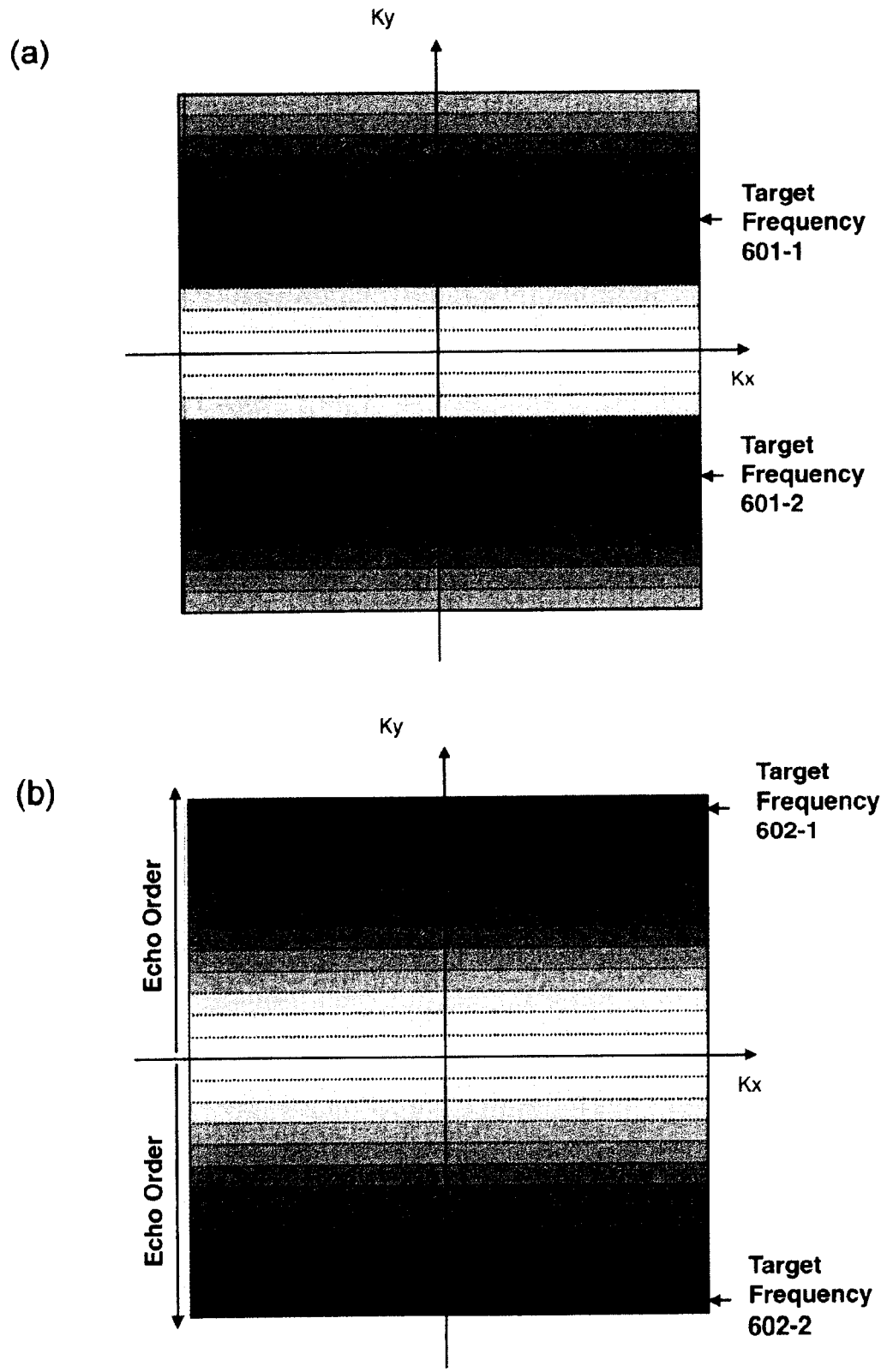
FIG. 6 is a diagram showing the arrangement of K space data in the measurement according to the first embodiment.
Figure 7:
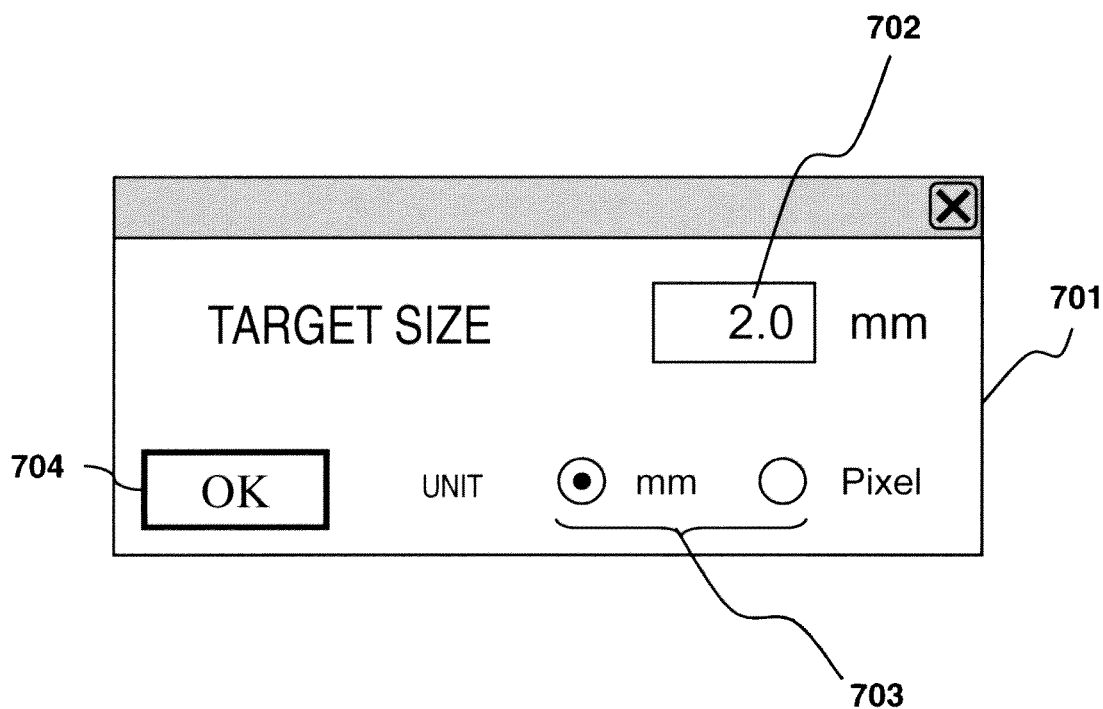
FIG. 7 is a diagram showing a target size setting window.
Figure 8:
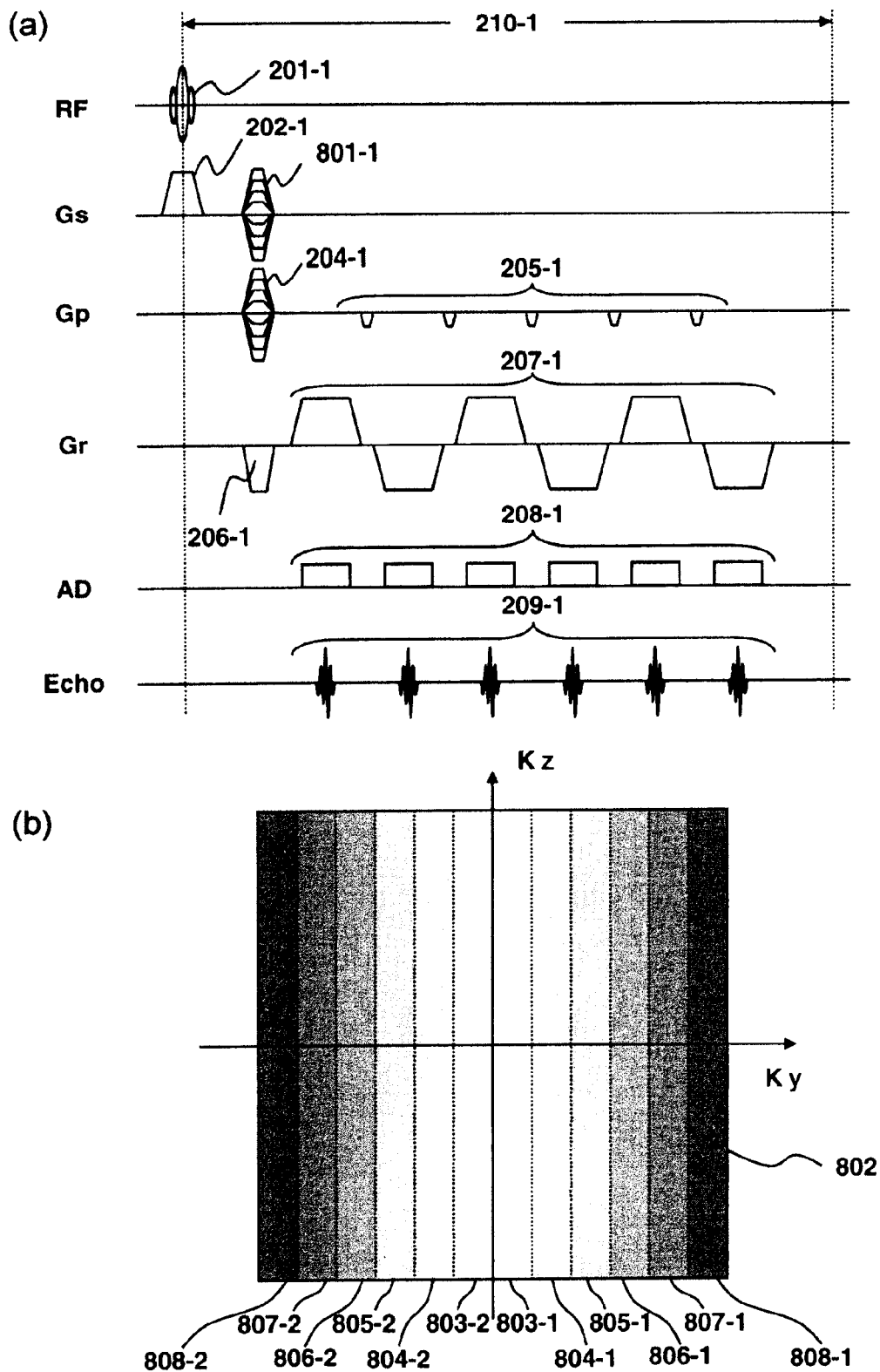
FIG. 8 shows (a) a three-dimensional sequence chart, and (b) K space data measured in the sequence according to a prior art.
Figure 1:
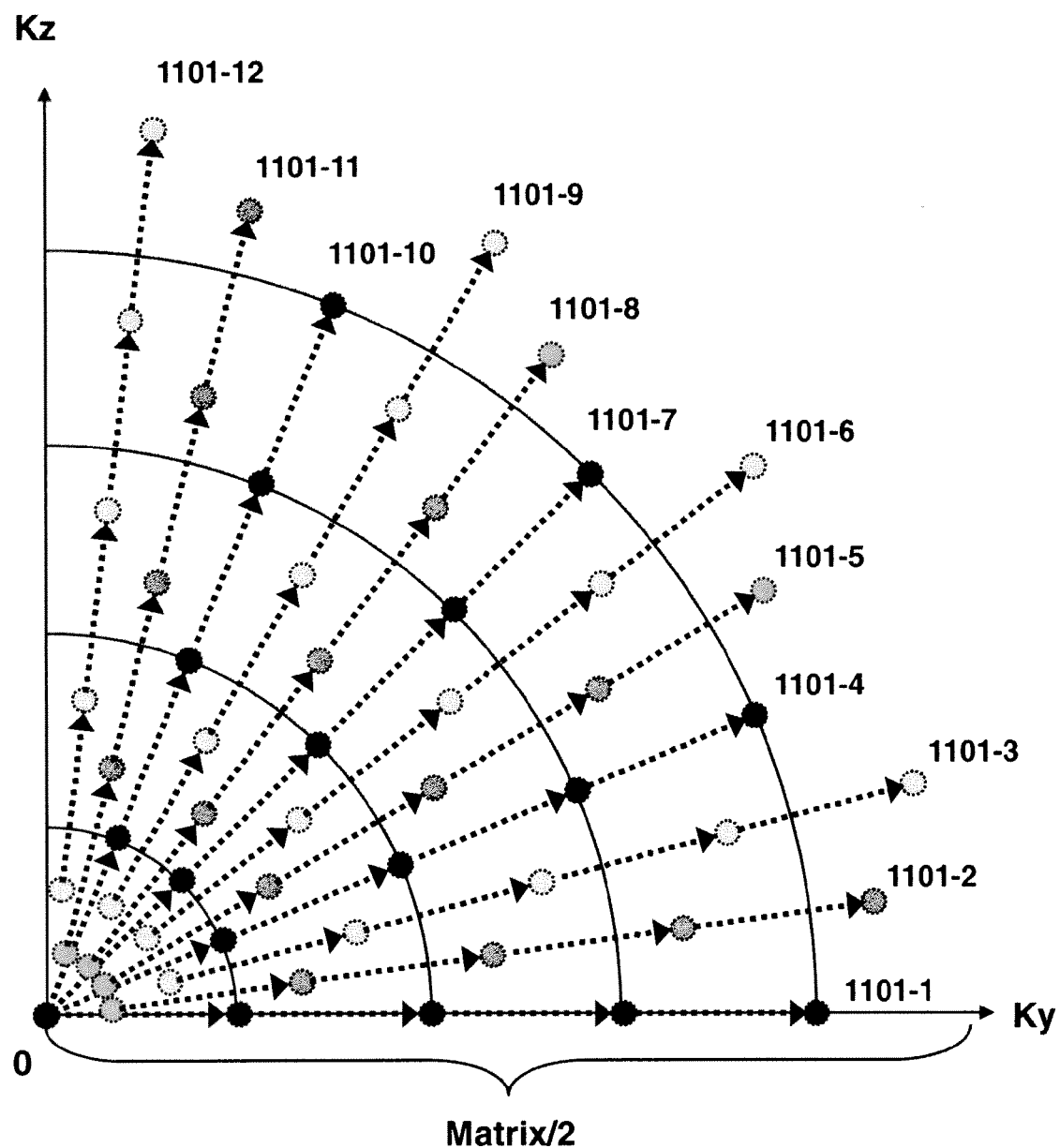
Figure 1:
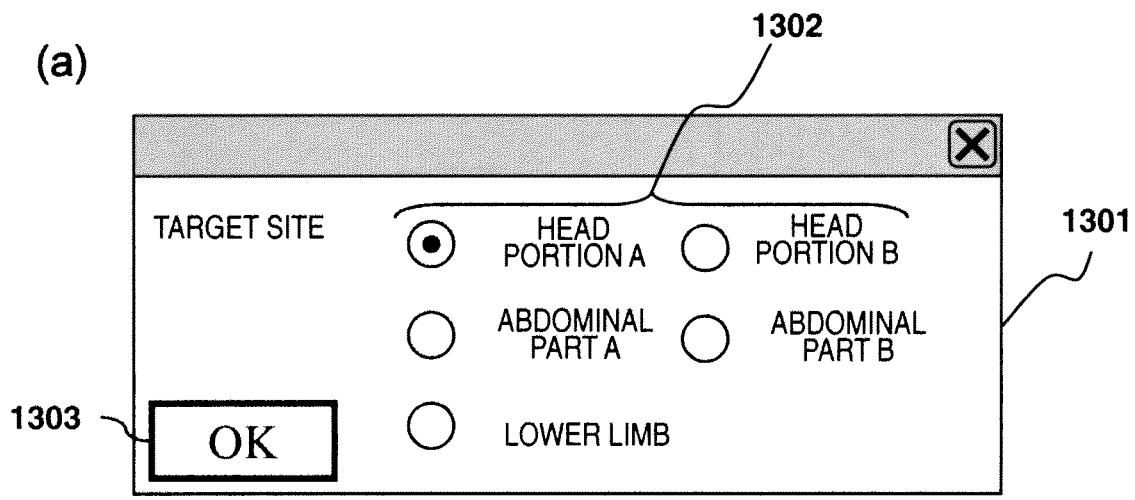

The invention claimed is:

1. A magnetic resonance imaging apparatus comprising:
a measurement controller configured to control measurement of plural echo signals from an examinee on a basis of a predetermined pulse sequence;
a gradient magnetic field generating unit that, under control of the measurement controller, applies a phase encode gradient magnetic field and a phase blip gradient magnetic field;
a calculation processor configured to obtain an image of the examinee on a basis of K space data including the plural echo signals; and
an operating system providing one or more input parts for interactive operator control to specify the imaging target site,
wherein the measurement controller sets a target size based on the operator-specified imaging target site, calculates a target frequency for the set target size, and sets a target echo time for the operator-specified imaging target site, wherein the measurement controller controls, based on the predetermined pulse sequence, the gradient magnetic field generating unit to apply the phase encode gradient magnetic field and the phase blip gradient magnetic field, and the measurement controller automatically sets applying amount of the phase encode gradient magnetic field and the phase blip gradient magnetic field based on the pulse sequence such that the echo signal which corresponds to the target frequency is measured at or near the target echo time.

2. The magnetic resonance imaging apparatus according to claim 1, wherein the measurement controller controls a measuring order of the plural echo signals to measure the echo signal corresponding to the target frequency at the target echo time.

3. The magnetic resonance imaging apparatus according to claim 2, wherein the calculation processor sets a spatial frequency within a range from an origin to a maximum spatial frequency in a phase encode direction (Ky) of the K space, to the target frequency.

4. The magnetic resonance imaging apparatus according to claim 2, wherein the pulse sequence is applied to measure the echo signals while applying the phase encode gradient magnetic field and the phase blip gradient magnetic field and reversing polarity of a frequency encode gradient magnetic field, and the measurement controller measures the plural echo signals by repeating the pulse sequence at least once.

5. The magnetic resonance imaging apparatus according to claim 4, wherein the measurement controller controls application of the phase encode gradient magnetic field and the phase blip gradient magnetic field and controls the measuring order of the plural echo signals.

6. The magnetic resonance imaging apparatus according to claim 4, wherein the pulse sequence is applied to measure the plural echo signals while alternately reversing the polarity of the phase blip gradient magnetic field.

7. The magnetic resonance imaging apparatus according to claim 1, wherein the K space is a three-dimensional space having a phase encode direction (ky) and a slice encode (Kz) direction, and the measurement controller controls the measuring order of the plural echo signals to measure echo signals corresponding to a spatial frequency area located in the same distance range from an origin of a Ky-Kz space at the same echo time range.

8. The magnetic resonance imaging apparatus according to claim 7, wherein the measurement controller selects a spatial frequency area located within a distance range from the origin of the Ky-Kz space as the target frequency, and controls the measuring order of the plural echo signals to measure echo signals corresponding to the selected spatial frequency area at the target echo time.

9. The magnetic resonance imaging apparatus according to claim 7, wherein the measurement controller sets to the target frequency a spatial frequency located at a distance from zero to a maximum spatial frequency from the origin of the Ky-Kz space.

10. The magnetic resonance imaging apparatus according to claim 7, wherein the pulse sequence is a three-dimensional pulse sequence for the phase encode gradient magnetic field and the phase blip gradient magnetic field, and a slice encode gradient magnetic field and a slice blip gradient magnetic field, and the measurement controller controls application of the phase encode gradient magnetic field and the phase blip gradient magnetic field, and the slice encode gradient magnetic field and the slice blip gradient magnetic field to control the measuring order of the plural echo signals.

11. The magnetic resonance imaging apparatus according to claim 7, wherein the measurement controller controls an application amount of at least one of the phase blip gradient magnetic field and the slice blip gradient magnetic field in a manner that the width in a radial direction of a spatial frequency area located in the same distance range from the origin of the Ky-Kz space is smaller at a high spatial frequency side than that at a low spatial frequency side.

12. The magnetic resonance imaging apparatus according to claim 1, further comprising a first input unit for inputting information on the size of the target area.

13. The magnetic resonance imaging apparatus according to claim 1, further comprising a storage unit for storing a table having information on a size of an area of interest of each imaging target site, wherein the calculation processor obtains the information on the size of the area of interest from the storage unit in accordance with the input information of the imaging target site.

14. A magnetic resonance imaging method performed by a magnetic resonance imaging apparatus, wherein said method performed by a magnetic resonance imaging apparatus comprises:
controlling, by a measurement controller of the magnetic resonance imaging apparatus, a gradient magnetic field generating unit of the magnetic resonance imaging apparatus to apply a phase encode gradient magnetic field and a phase blip gradient magnetic field, based on a predetermined pulse sequence, and measuring plural echo signals from an examinee;
obtaining an image of the examinee on a basis of K space data including the plural echo signals;
receiving interactive operator control specifying the imaging target site through one or more input parts of the magnetic resonance imaging apparatus;
operating by the measurement controller of the magnetic resonance imaging apparatus to set a target size based on the operator-specified imaging target site, calculate a target frequency for the set target size, and set a target echo time for the operator-specified imaging target site; and
setting automatically, by the measurement controller based on the pulse sequence, amount of the phase encode gradient magnetic field and the phase blip gradient magnetic field such that the echo signal which corresponds to the target frequency is measured at or near the target echo time.

15. The magnetic resonance imaging method according to claim 14, wherein the measuring step controls a measuring order of the plural echo signals to measure the echo signal corresponding to the target frequency at the target echo time.

* * * * *